(12) United States Patent
Turgeon

(10) Patent No.: US 6,613,960 B1
(45) Date of Patent: Sep. 2, 2003

(54) PHLOEM-LOADING-SPECIFIC PROMOTER

(75) Inventor: E. Robert Turgeon, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/503,890

(22) Filed: Feb. 15, 2000

(51) Int. Cl.$^7$ .......................... A01H 1/00; C12N 15/82; C12N 5/00; C07H 21/04

(52) U.S. Cl. ................... 800/278; 536/24.1; 435/320.1; 435/410

(58) Field of Search .............................. 536/23.1, 23.6, 536/24.1; 435/69.1, 320.1, 410; 800/278

(56) References Cited

U.S. PATENT DOCUMENTS

| | | |
|---|---|---|
| 5,034,322 A | 7/1991 | Rogers et al. |
| 5,602,321 A | 2/1997 | John |
| 5,648,210 A | 7/1997 | Kerr et al. |
| 5,750,385 A | 5/1998 | Shewmaker et al. |
| 5,773,699 A | 6/1998 | Kerr et al. |
| 6,002,068 A | 12/1999 | Privalle et al. |

FOREIGN PATENT DOCUMENTS

| | | |
|---|---|---|
| WO | WO 93/02196 | 2/1993 |

OTHER PUBLICATIONS

DeWitt et al., "Evidence for a Plasma Membrane Proton Pump in Phloem Cells of Higher Plants," *The Plant Journal*, 1:121–128 (1991).
Martin et al., "Expression of an Arabidopsis Sucrose Synthase Gene Indicates a Role in Metabolization of Sucrose both During Phloem Loading and in Sink Organs," *The Plant Journal*, 4:367–377 (1993).
Riesmeier et al., "Evidence for an Essential Role of the Sucrose Transporter in Phloem Loading and Assimilate Partitioning," *The EMBO J.*, 13:1–7 (1994).
Sauer et al., "SUC1 and SUC2: Two Sucrose Transporters from *Arabidopsis thaliana*; Expression and Characterization in Baker's Yeast and Identification of the Histidine–Tagged Protein," *The Plant Journal*, 6:67–77 (1994).
Lerchl et al., "Impaired Photoassimilate Partitioning Caused by Phloem–Specific Removal of Pyrophosphate Can Be Complemented by a Phloem–Specific Cytosolic Yeast––Derived Invertase in Transgenic Plants," *The Plant Cell*, 7:259–270 (1995).
Truernit et al., "The Promoter of the *Arabidopsis thaliana* SUC2 Sucrose–H$^+$Symporter Gene Directs Expression of β–Glucuronidase to the Phloem: Evidence for Phloem Loading and Unloading by SUC2," *Planta*, 196:564–570 (1995).
Shimojima et al., "Cloning of the Gene for Monogalactosyldiacylglycerol Synthase and Its Evolutionary Origin," *Proc. Natl. Acad. Sci. USA*, 94:333–337 (1997).
Kühn et al., "Macromolecular Trafficking Indicated by Localization and Turnover of Sucrose Transporters in Enucleate Sieve Elements," *Science*, 275:1298–1300 (1997).
Bürkle et al., "The H$^+$–Sucrose Cotransporter NtSUT1 Is Essential for Sugar from Tobacco Leaves," *Plant Physiol.*, 118:59–68 (1998).
Pool, "In Search of the Plastic Potato," *Science* 245:1187–1189 (1989).
Haritatos, "Raffinose Oligosaccharide Concentrations Measured in Individual Cell and Tissue Types in *Cucumis melo* L. Leaves: Implications for Phloem Loading," *Planta* 198:614–622 (1996).
Haritatos, "Minor–Vein Phloem in *Cucumis melo* L. and *Arabadopsis Thaliana*: Testing a Model and Developing New Tools," Mann Library, Cornell University, catalogued Feb. 19, 1999.

*Primary Examiner*—Sean McGarry
*Assistant Examiner*—Janet Epps-Ford
(74) *Attorney, Agent, or Firm*—Nixon Peabody LLP

(57) ABSTRACT

The present invention relates to DNA promoters which, in nature, drive expression of an enzyme of the raffinose family oligosaccharide pathway and are capable of inducing expression of a protein encoded by a DNA molecule operably associated with such promoters. These DNA promoters cause the protein to be expressed in minor vein phloem of a mature plant leaf, with substantially no expression of the protein elsewhere in the leaf of the plant. The present invention also relates to the use of such DNA promoters in transgenic plants or plant seeds.

44 Claims, 4 Drawing Sheets

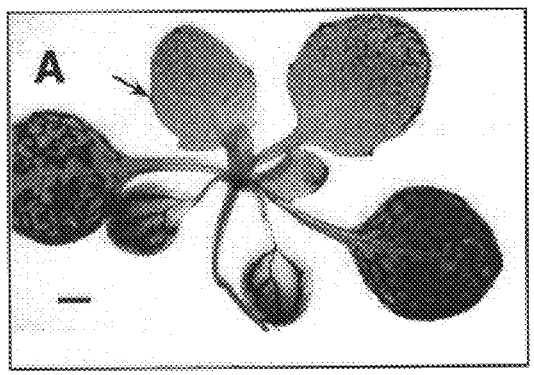
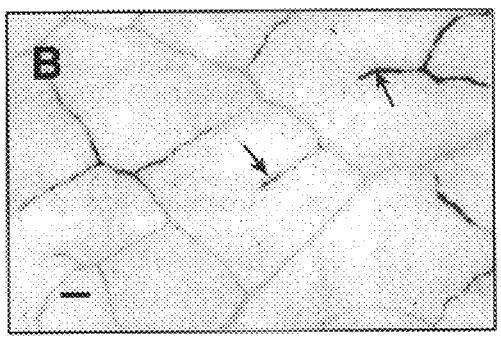
FIG. 3A     FIG. 3B
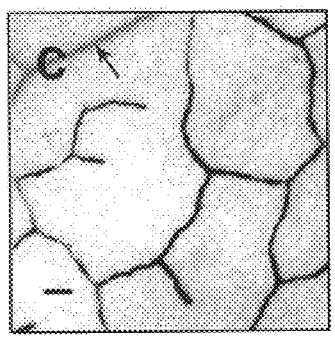
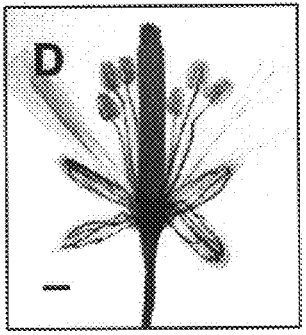
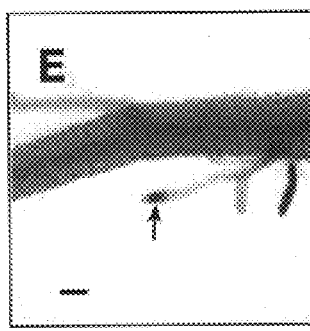
FIG. 3C     FIG. 3D     FIG. 3E
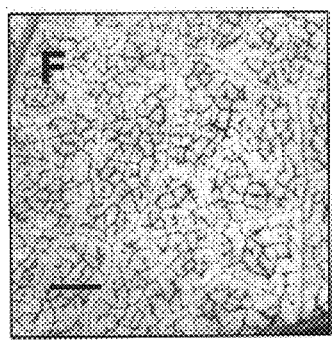
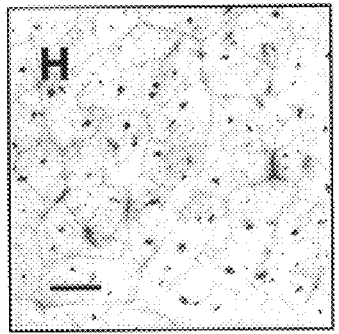
FIG. 3F     FIG. 3G     FIG. 3H
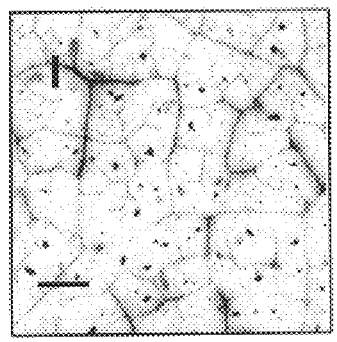
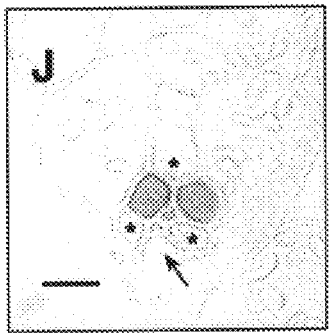
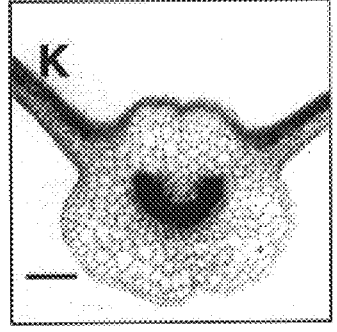
FIG. 3I     FIG. 3J     FIG. 3K

PHLOEM-LOADING-SPECIFIC PROMOTER

This invention was developed with government funding by the USDA-NRI Competitive Grants Program, Grant No. 9801617. The U.S. Government may have certain rights.

FIELD OF THE INVENTION

This invention relates to a phloem-loading specific DNA promoter used to drive the expression of heterologous genes in minor vein phloem of transgenic plants.

BACKGROUND OF THE INVENTION

Genetic engineering of plants, which entails the isolation and manipulation of genetic material (usually in the form of DNA or RNA), and the subsequent introduction of that genetic material into plants or plant cells, offers considerable promise to modem agriculture and plant breeding. Increased crop values, higher yields, feed value, reduced production costs, pest resistance, stress tolerance, drought resistance, the production of pharmaceuticals, chemicals and biological molecules are all potentially available through genetic engineering techniques.

Methods for producing transgenic plants are well known. In a typical transformation scheme, a plant cell is transformed with a DNA construct, in which a "foreign" DNA molecule that is to be expressed in the plant cell is operably linked to a DNA promoter molecule, which will direct expression of the foreign DNA in the host cell, and to a 3' regulatory region of DNA that will allow proper processing of the RNA transcribed from the target DNA. The choice of foreign DNA to be expressed will be based on the trait, or effect, desired for the transformed plant. The promoter molecule is selected so that the foreign DNA is expressed in the desired plant. Promoters are regulatory sequences that determine the time and place of gene expression. Transcription of DNA is dependent upon the presence of a promoter which is a DNA sequence that directs the binding of RNA polymerase and thereby promotes mRNA synthesis.

Generally there are two types of promoters, constitutive and inducible. A constitutive promoter is a promoter that directs expression of a gene throughout the various parts of a plant and continuously throughout plant development. Examples of some constitutive promoters that are widely used for inducing the expression of heterologous genes in transgenic plants include the nopoline synthase (NOS) gene promoter, from *Agrobacterium tumefaciens*, (U.S. Pat. No. 5,034,322 to Rogers et al.), the cauliflower mosaic virus (CaMv) 35S and 19S promoters (U.S. Pat. No. 5,352,605 to Fraley et al.), those derived from any of the several actin genes, which are known to be expressed in most cells types (U.S. Pat. No. 6,002,068 to Privalle et al.), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. In addition, inducible promoters include promoters that function in a tissue specific manner to regulate the gene of interest within selected tissues of the plant. Examples of such tissue specific promoters include seed, flower, or root specific promoters as are well known in the field (U.S. Pat. No. 5,750,385 to Shewmaker et al.).

In order to maximize the commercial application of transgenic plant technology, it is important to direct the expression of the introduced DNA in a site-specific manner. For example, it is desirable to produce toxic defensive compounds in tissues subject to pathogen attack, but not in tissues that are to be harvested and eaten by consumers. By site-directing the synthesis or storage of desirable proteins or compounds, plants can be manipulated as factories, or production systems, for a tremendous variety of compounds with commercial utility. Cell-specific promoters provide the ability to direct the synthesis of compounds, spatially and temporally, to highly specialized tissues, such as the leaf vascular system of plants.

The vascular system of the leaf is distributed throughout the blade. The vascular strands form an interconnected system in the median of the blade parallel with the surface of the leaf. The vascular bundles in the leaf are commonly called veins, and the pattern formed by these veins, venation. Leaf venation occurs in two main patterns, the reticulate, or netted, and the parallel. Reticulate venation may be described as a branching system with successively thinner veins diverging as branches from the thicker veins. In the parallel-veined leaf strands, strands of relatively uniform size are oriented longitudinally, or nearly so. Netted venation is most common in dicotyledons, parallel venation in monocotyledons.

Leaves with reticulate venation often have the largest vein, the midvein, along the median longitudinal axis of the leaf. The midvein is connected laterally with somewhat smaller lateral veins. Each of these is connected with still smaller veins, from which other small veins diverge. The ultimate branchings form meshes delimiting small areas of mesophyll, the main photosynthetic tissue of the leaf. In dicotyledons, the smaller veins are embedded in the mesophyll. The smaller veins, known as minor veins, play an important role in transport of food and water. They distribute the transpiration stream through the mesophyll and serve as starting points for the uptake of the products of photosynthesis and their translocation out of the leaf.

The outstanding characteristics of minor veins is the prominence of vascular parenchyma cells, particularly those in the phloem, the principal food-conducting tissue of the vascular plant. Parenchymal cells generally have dense protoplasts and numerous plasmodesmata of the branched type, which provide a cytoplasmic interconnection with sieve elements, a cell of the phloem tissue which is concerned with the longitudinal conduction of food materials. Sieve elements are classified into sieve cells, and sieve tube members. Another important cell located in minor veins are companion cells, a type of parenchyma cell closely associated with sieve elements and with the translocation of food material. Intermediary cells are companion cells of minor veins that are found only in plants that export raffinose-family oligosaccharides (RFOs). All these cell types are involved in the process of phloem loading of the minor veins. Esau, "Plant Anatomy," New York: John Wiley and Sons (1965).

Phloem loading is the process in which the products of photosynthesis accumulate to high concentration in preparation for export. Early research on translocation provided much evidence that movement of organic materials in the phloem depends on the physiologic interaction between sieve elements and the contiguous parenchymal cells. In tissues where sugars become available for transport, such as photosynthesizing leaf mesophyll or reactivated storage parenchyma, sugars are transmitted to the conduits (loading of sieve elements) by the contiguous parenchyma cells. At sites of utilization of sugars, that is, wherever growth occurs or storage materials are sequestered, parenchymal cells remove sugars from the conduit (unloading of sieve elements). Thus, the phloem is an integrated system of conduits and contiguous cells concerned with the loading and unloading of the conduits along the path of translocation at sites of sources for sugars and sinks for the same.

The site of the loading and unloading of sugars changes in a foliage leaf as the leaf matures. The sink-source transition marks a major shift in leaf structure and physiology, leading to a reversal in the polarity for phloem transport. This transition occurs in dicotyledonous species when the lamina is approximately 30–60% expanded. It involves an orchestrated series of developmental events that leads to cessation of phloem unloading in moderately sized veins, initiation of phloem loading in minor veins, and an overall switch from catabolic to anabolic metabolism, resulting in production of transport sugars for export. Turgeon R., "The Sink-Source Transition in Leaves," *Ann. Rev. Plant Physiol. Plant Mol. Biol.* 40:119–138 (1989). A particularly interesting anabolic pathway turned on at the time of the sink-source transition is the one leading to raffinose family oligosaccharide (RFO) synthesis. RFO's are translocated in certain species, such as the cucurbits, that phloem-load symplasmically. Turgeon R., "Phloem Loading and Plasmodesmata," *Trends in Plant Science* 1:403–441 (1996).

Many promoters have been described that are phloem-specific to a greater or lesser degree. Among these, several have been reasonably well-characterized. Not surprisingly, promoters that drive expression of sucrose transporters are highly active in source leaf phloem since these proteins are involved in phloem loading (Stadler et al., "Phloem Loading by the PmSUC2 Sucrose Carrier from *Plantago major* Occurs into Companion Cells," *Plant Cell* 7:1545–1554 (1995). However, sucrose symport activity is widespread, perhaps ubiquitous, in plant tissues; as a result, these promoters are active in the phloem of several tissue types. The SUC2 promoter, for example, directs β-glucuronidase (GUS) expression to the phloem of stems and roots, in addition to that of leaves and sepals. Furthermore, under SUC2 promoter direction, activity is found in all veins within the leaf, not just the minor veins. Truernit et al., "The Promoter of the *Arabidopsis Thaliana* SUC2 Sucrose-H+ Symporter Directs Expression of Beta-Glucuronidase to the Phloem: Evidence for Phloem Loading and Unloading by SUC2, " *Planta* 196:564–570 (1995). Studies with another sucrose/H+symporter, as well as one H+/ATPase promoter region indicate expression in major (large) veins and sink tissue as well as in minor veins. DeWitt et al., "Evidence for a Plasma Membrane Proton Pump in Phloem Cells of Higher Plants," *Plant J.* 1:121–128 (1991), Kühn et al., "Macromolecular Trafficking Indicated by Localization and Turnover of Sucrose Transporters in Enucleate Sieve Elements," *Science* 275:1298–1300 (1997).

The discovery of new tissue-specific promoters is desired for the controlled expression of heterologous DNA genetically engineered into transgenic plants. While other phloem-associated promoters have previously been identified, none have been found to be phloem-loading specific for the minor veins of the mature leaf.

The present invention is directed to overcoming these and other deficiencies in the art.

SUMMARY OF THE INVENTION

This invention relates to the isolation of a DNA promoter which is capable of inducing the expression of protein-encoding genes in minor vein phloem of plants, with substantially no expression of the protein occurring elsewhere in the plant leaf.

This invention also relates to a method of directing protein expression in minor-vein phloem of a plant, wherein the phloem-specific DNA promoter is associated with a DNA which encodes for either an endogenous or heterologous plant protein, such that expression of the DNA molecule, under control of the DNA promoter, is expressed in the minor-vein phloem of a plant, with substantially no expression of the protein occurring elsewhere in the plant leaf.

This invention also relates to transgenic plants and seeds produced by transformation with the DNA construct consisting of the phloem-specific DNA promoter and a DNA encoding a protein.

One aspect of the present invention relates to the isolation of a phloem-loading specific DNA promoter, which is capable of inducing the expression of protein encoding genes in minor-vein phloem of plants. The promoter would also be useful in producing compounds for transport to other parts of the plant for storage or metabolism. In this type of application, leaf companion cells, with direct access to the energy resources of the photosynthetic cells, would be factories, producing materials for accumulation in other tissues. These could be natural or entirely synthetic compounds. As an example, plastic precursors have been produced in leaf cells of other plants, but they often cause the plants to be severely stunted. If toxic compounds such as these were produced in the companion cells of leaves and then immediately transported to other organs, such as the roots, they might cause much less growth inhibition and yield would be improved.

Thus the present invention provides a highly specific tool for the site-directed expression of heterologous DNA in plants, increasing the potential for commercial application of plants as high-output production systems for desirable proteins or compounds, and overcoming the deficiencies of the constitutive or less-specific inducible promoters currently used for plant genetic engineering.

Both nptII and uidA coding regions are fused to the nopaline synthase polyadenylation signal (nos-ter). The right and left T-DNA borders are denoted RB and LB Arrows indicate direction of transcription.

FIGS. 3A–K show the staining patterns of Arabidopsis (FIGS. 3A–3E) and tobacco (3F–3K) transformed with the galactinol synthase promoter GAS-GUS construct pSG3K101. FIG. 3A shows a fourteen-day old seedling. Staining is dense in the minor veins of leaves and cotyledons. Veins at the tips of three developing leaves are stained in the same pattern as the sink-source transition. Hydathodes also stain (arrow). Bar=1 μm. FIG. 3B shows a mature leaf tissue stained for 3 hours. Staining is most apparent in the blind endings (arrows) and other small veins. Bars=200 μm. FIG. 3C: after 24 hours, all minor veins are stained. A secondary vein (arrow) is unstained. Bar=200 μm. FIG. 3D shows a flower in which stain is visible in the filaments, in veins of the sepals, and less intensely in those of the petals. Bar=0.5 mm. FIG. 3E shows faint blue staining near the tip of a branch root. Bar=0.5 mm. FIG. 3F shows leaf tissue near the tip of a growing leaf that has completed the sink-source transition. The vein in the lower right hand corner is the midrib, the one in the upper left is a secondary. Bar=1.8 mm. FIG. 3G shows veins of a mature leaf. The vein classes are numbered. Note the partial staining of a Class IV vein at the junction of a Class V vein (arrow).

There is no diffusion of stain from the vein marked with an asterisk. Bar=400 μm. FIG. 3IH shows the staining pattern of immature veins in the proximal region of a leaf undergoing the sink-source transition. Bars=300 μm. FIG. 3I: tissue from the same leaf as FIG. 3H, but more distal and mature. Bars=300 μm. FIG. 3J shows the localization of stain in a transverse section. Two companion cells, and the small sieve element between them, are stained. The third companion cell (arrow) and its sieve element are unstained. Phloem parenchyma cells are indicated by asterisks. Bar=10 μm. FIG. 3K shows a transverse hand section through the midrib. Stained minor veins can be seen in the flanking lamina, but the vascular tissue of the midrib is unstained. Bar=0.6 mm.

Figure 4A:
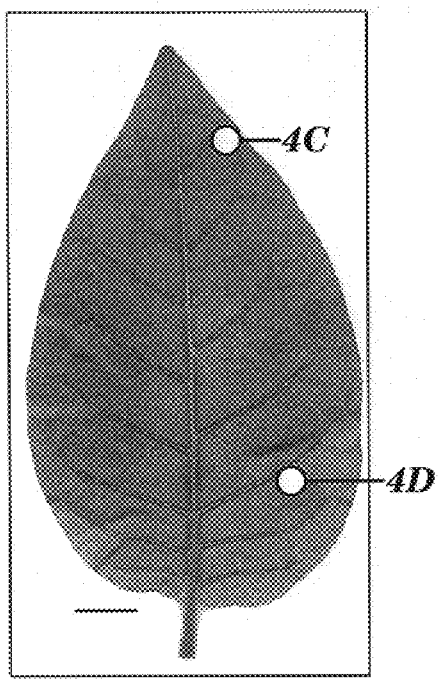
Figure 4B:
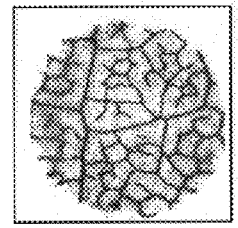
Figure 4C:
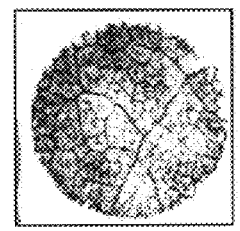
Figure 4D:
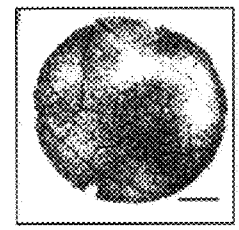

FIGS. 4A–D demonstrate phloem loading in leaf discs exposed to [$^{14}$C]sucrose in plants transformed with the galactinol synthase promoter (GAS)-GUS construct pSG3K101. FIG. 4A shows a developing tobacco leaf the same size as the leaf used for the $^{14}$C-labeling experiments. Leaves of this age have just ceased importing photoassimilate from mature leaves. In developing leaves there is a basipetal gradient in maturity, the distal end being more mature than the base. Bar=1.5 cm. FIG. 4B is an autoradiograph of a disc from a fully expanded, mature leaf. The disc was exposed to a [$^{14}$C]sucrose solution prior to freeze-drying. [$^{14}$C]sucrose has accumulated in the veins. FIG. 4C is an autoradiograph of a disc excised near the tip of a developing leaf, as indicated by the arrow. [$^{14}$C]sucrose has accumulated in the veins, though not to the same degree as in mature leaf tissue. GUS staining, as illustrated in FIG. 3H, was visible from tissue adjacent to this disc, but not in more proximal tissues. FIG. 4D is an autoradiograph of a disc excised near the base of a developing leaf, as indicated by the arrow. This is the most proximal tissue in which [$^{14}$C] sucrose accumulated in the veins. No GUS staining was evident in adjacent tissue. Bar in B–D=1 mm.

DETAILED DESCRIPTION OF THE INVENTION

This invention relates to the isolation of a phloem-loading specific DNA promoter, which is capable of inducing the expression of protein encoding genes in minor-vein phloem of plants.

This invention also relates to a method of directing protein expression in minor vein phloem of a plant, wherein the phloem-specific DNA promoter is associated with a DNA molecule which encodes for either an endogenous or heterologous plant protein, such that the protein encoded is expressed in the minor-vein phloem of a plant transformed with such a DNA construct.

The DNA construct includes a DNA molecule which is the phloem-loading promoter, an operably linked protein-encoding DNA molecule, and a 3' regulatory region operably linked to the protein-encoding DNA molecule. As discussed more fully hereinafter, a DNA construct of the present invention is particularly useful in preparing a transgenic plant for the purpose of rendering the transgenic plant a production system for the expression of a DNA of choice in the minor vein phloem of a plant.

The DNA promoter molecule in the construct of the present invention is a phloem-loading specific promoter. One form of the promoter of the present invention is the GAS promoter isolated from *Cucumis melo* (melon), which has a nucleic acid sequence corresponding to SEQ. ID. No. 1 as follows:

−3140
    GAGCTCCACC GCGGTGGCGG CCGCTCTAGA ACTAGTGGAT

−3100    CCCCCGGGCT GCAGGAATTC TAGAT-GACTT GGATTAATTC TCTAACAAGA

−3050 ATTTAGTTTA ATTGACATTT GTATGTTTGA GGACTAAGAG GACTTTAGTT

−3000 TTAATTTCTA ATCTAATTTG TACTAGAAAA GAAAAAAAAA GAGTCGGATT

−2950 AATTCTCTAC CATTGAGTGG AGGATACTTG GATGCAGTTC AAGTTCTCAT

−2900 CTCTCCAATT TGTCACGTGA CAGCG-GATGA TTAAGCATAT GAGTAGGCTG

−2850 CAAAAGATTA TAGACGTAGA AGAT-GATACC AATACAAAG GCGTAACTTT

−2800 TCCCGGATGA CTTTTATACT CTTTACAAAA TTGGAAGTCC TATTCTATCT

−2750 ACATCTTAAT TTCCAGTTGT TATAATGAAG AATAGTCTGA AAATGATATC

−2700 AATTTTTTCT TTCTCAATAC CATTCAATTA CGTTAAGATT ATTAGGAGCT

−2650 GCCATTATTA TTATTATTAT TGTTGTTGTT ATTATTATTA TTATGCAACC

−2600 AAGTTTGATT TGAAATTGTT TGCCAAATTT TACTCCAATT TGATGTTGTT

−2550 TAATTACTTT AGATGGTATA ATAAGAATGA AGTTGAATTT AAAGAAAAGA

−2500 AACAAAGCTT GAAAGAATGG AATACT-TAGG TGTAGAAGAA GACAACGTAT

−2450 TTATAACGTC GTATAGTGTT AATAAAAATG CACACATTTG GATGCCCTTT

−2400 ATGCTTTCTT AGAGGTCAGA CTTTCCCACA AAGGCTAAGG TGATTCAATC

−2350 GTGTGGGACA TCTTGTTCTC CCATTTGATT CTCGTTTTCA TTAGACCAAA

−2300 ATTAACAAAA AAATAGTAAT AATTCTATTC TTTTTAAAGT TTGTGATATT

−2250 ACGGTTTATC CTTTGTTAAA AAAGTTTATC TTTGAATGTA AGAATTTGAT

−2200 AGAATGTTGA ATGAAAATTA AGATTTTGAA AAGTTTTGCT GAATTTCAAA

−2150 TAATATAACT CTCTAACTTT GGTTTAGGAA AATTAAGTGA TGACAATTAT

-2100 CTCTATTAGA ATTAGTATTA TAAGTGATAT TTGAGTTATG CACTTGACTT

-2050 GGTCGTGTTG GTAAATTCTT TGGATACAGA ACAAAAGAAG TTGCATGCCA

-2000 AGAAAGATTT CTAATAGATA TGGTGAGATA TGTGGCCGTT GGCTCTATTG

-1950 GATTGGTGGT ATGTTCCAGA GAAGAGGAGT GCGTATGGAT ACGACCTAGG

-1900 TGGATAAATG ATTATATGAG GAGATGGTAA TTTTATGAAA TGTGTTAGAG

-1850 CTTTGATGTT AATATATATT TTTTAAGTGT GTTTTGTGAT CGATGGTATT

-1800 AGATGAGTTC CTTATTAAAC ATGTTTTCTT GTTTTTCTCG AGGTGGGGTT

-1750 CTCAACACTT GGTAACATGC ATCATGTCCA CGAGATGTTC TTCATCTTAT

-1700 CTCTTGTAAT ATTATATATG ATATCTCACA CAATACAGGT TCGTCTGAAA

-1650 AATCTTTCTT TATTTGAAAT TTTTTAGGTA TTTATTCTTG AGGATTTTTT

-1600 TATTCTTAAG TAAAGTGTTC ATGATTTGAA GTTAGAAATA TAGGAGTTAT

-1550 TTTTAAGAGA GAGTCTCACA CTCAAAGGGA GTCTAAATAT CTTTTTTACT

-1500 AATTTAGGTT GTGTAATAAC CTTGTATTTA TCGATAAGTA TCACGATGTA

-1450 ATCATTTAAC TATCTATTAA CGAAAATCTT TTTTAGGACA CGTTGCCTCC

-1400 TAGATAGATG CAAGTTGTAT TGCAAAACTT GTACTCTGTT TTTTAGTTTT

-1350 TTACATGTTT TACTTTAGAA CTAAACCTAA GTTATGTTAT GTGTCAAATA

-1300 AACTTCTTTA AAATAATATT AAAACTTCTC AAAATAATAG GAAAAAAAAG

-1250 AAAAATTTCA AATTTAATAT ATATATATAT ATATTGTAAT ATTAGCTTTC

-1200 ATTATCATTG AATTAAAAAT TGCATATACA AGAATCGAAT AATGTGGAGA

-1150 AAGTAGTTTT CCTTTTTCAA CTTTGTGTAG AGGCTAAGTC TCTAAAATAT

-1100 TGGCTTCGAC TTTGTACTTT TGGGATCCGC CACCACAATC AGACAAACTT

-1050 CCATTTGATC ATTACCTTTA TCGAATCAAA TTCTTTCCCT TCCAATCTGT

-1000 CACAATTTTG AACATACCAT CCACCTTCTG ATTTTTTGAT TCTAAATAAA

-950 CCTTATTAGC AGAGATTTTT AAAATTAGTA TTAAATTATA CCAAATACCC

-900 TAATGAACTT TTTCAATAGT TTTTCTATTT TATTTTTTTT TTCTTTTGTG

-850 TGTATGAGTT TTTTCACCAC CATTAGAAAA CACATTTGAA ATATACAGAA

-800 CCAAATTGTT TAATTTGAAT TGGTTTTCCA TACCATTTTT ACAAAATACA

-750 TAGTATAACC AAAAGAACTA TAGTTTTAAG TAGTGTATAA TAGTTTAATT

-700 TTAAAGACAA AGAACTAAAC AATAATCATT ATCAAAAACA CTACCTTAAA

-650 ACAGAATTGA AATCAAATCC ATTTGTTTAG GAATATATAT ATATATATAT

-600 ATATATATAA TATAGTATCA TAATATATAA AAAAAATGTC AAAATCTGAG

-550 ATTCTTTGAT CCTCCCTAAA TTGTCCATTT TTGTCTTGCC TACAAACTTG

-500 CAAAAAAGAA AAAAAAAAAG GTTCATAGAT AGAAATGACC CATAATTGAA

-450 TCATAAAGCA ATAAGGATAT ACAAAATTAT TATATCCAAG AGGGATGAGA

-400 GATAATCTTA AAGGTGCAAA AGAATCTTCT TATTGATGGA AGAAGAGAAT

-350 ACAAACTCTT CCAACTTTTG ATCAAAATGC CCATAATGCC CTCCATCTCA

-300 CCTTAAAGAT AGGATATTCC AAGTCATATT CATCCCACCA ATACCAATAT

-250 CTAAAATAAT AAGTAACAAA TAATTACAAT TACAAATATA AAGTGCATAG

-200 AAATTAAACT TAGGGGTATG TATAAACTTA AAACAATGTT CCCCAAGGCT

-150 CTATAAATAG CCTCCTTCCC ATCCCTTCAC AACTCAAGCT TGAAGGACTA

-100 AAACAAGAAC TTGTAAGCTT GCCCTTCTTA TTAAGTCCTT CTTGCCTCCC

-50 TTCCTTCGGA GAGAAAAAAC TTTTGTTGTT TCAAAAGCAC CAAAGTCAAT

+1 ATGTCTCCTG CAGCTGCCCC AGAAAGTGCC ATTGAGTCAA CTGACGCTCC

+51 CAAGAGGGCG TACGTGACGT TCTTAGCTGG TAATGGTGAC TACTGGAAAG

+101 GTGTAGTTGG ATTGGCAAAG GGTCTCAGAA AGGTCAAAGC CGCCTACCCT

+151 CTCATTGTCG CTGTCCTTCC TGATGTTCCT GAAGATCATC GCCAATCCTC

+201 GAG

The galactinol synthase start codon (ATG) marking the 3' terminus of the promoter is in boldface. The untranslated leader region is shown as negative numbers prior to the translated promoter region, which is represented by nucleotides +1 to +201. The underlined sequence is from the multiple cloning site of pBluescript II KS+ (Stratagene, LaJolla, Calif.).

Figure 1:
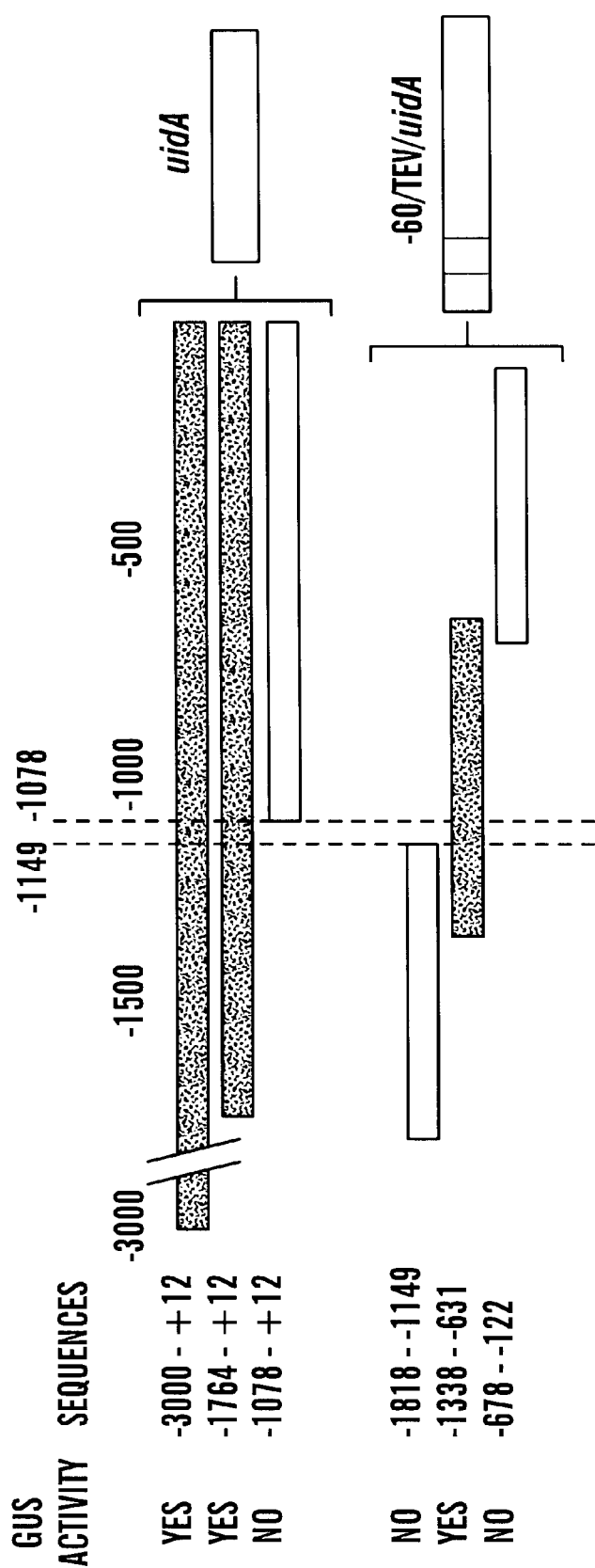
FIG. 1 is a diagram showing the expression of GAS1 promoter truncations in transgenic Arabidopsis plants. The bars represent different lengths of the promoter sequence obtained by truncation. Solid bars represent truncations that provide standard minor vein expression, open bars are not active at all. Note that there is no expression from the third or fourth constructs, implying that the region between them (−1078 to −1149; dashed lines) is present in active constructs. This is supported by the fifth construct which crosses this region and is active.

Fragments of the nucleotide sequence given as SEQ. ID. No. 1 which induce expression of heterologous DNA in transgenic plants are also suitable promoter DNA sequences for use in the DNA construct of the present invention. The isolated DNA corresponding to SEQ. ID. No. 1 can be truncated at various points and inserted into the construct of the invention. Several fragments show promoter activity, including fragments containing nucleotides −1764 to +12, and nucleotides −1338 to −631 of SEQ. ID. No. 1. When fragments from either side of, but not including, the 71 bases from −1149 to −1078 of the GAS promoter are tested in the construct of the present invention, no promoter activity is observed. FIG. 1 shows the truncated promoter sequences substituted into the vector and their ability to induce GUS expression. This data indicates that the nucleotide sequence from −1149 to −1078 is necessary, but may not be sufficient, for minor vein expression.

A second promoter in accordance with the present invention is also found in *Cucumis melo*. This promoter, known as GAS2, shows a high degree of homology with the GAS1 nucleotide sequence. Pair-wise matching between 3000 nt of GAS2 and 71 nt of GAS1 found greater than 50 regions with homologies exceeding 6 nt. The program used was MACAW (Multiple Alignment Construction & Analysis Workbench). The GAS2 promoter has a nucleic acid sequence corresponding to SEQ. ID. No. 2 as follows:

-3005 TAGTTCCGGT CCTGCNAGAC TGGC-
CCCCGC TCGAAACCTC CCTGGGTGTG AGGG-
TAGGAT
-2945 TGTCCACATT ATGGACCGTC TCATTCTCTC
TCTATGTCGT TCTCGTTAGT ATCAACTTGC
-2885 AACTTGTATT ACGCTAGCAA TTATAACGAC
TCACCAAAAT TTACTTCTTC ACTACTTCTT
-2825 CACGTATCTC TTATTTGAAG
AAAAAAAAGT AAAAATAAAA TATAAGTTAT
ACATAGCATA
-2765 TCCGAAGTGA TTCTAAAATA AGTAAAATCA
CTTTGAATCA CACTTTTAAT CATTCAAGAC
-2705 CTATTTAATG TTTAATCTTT AGATTTTTAT
ATATACTTTT CATATGGTTA AAATTAATTT
-2645 TAAATGATTA AAAGAAATTT TCAAGTGATT
TTGACCATTT TAAAATAGTT ATGCCCAAAT
-2585 ATATCATTAC ACATCTCTTA ATTTTTCAAG
TTCGAAGAGT TTTGAAGAAT TTGTTTTCTC
-2525 AACATGATGG GCTCCCCCTC TTGTCCCCTC
TCAAAGCCAT CATTTATCAA GTGAAAGAAT
-2465 TGCACTTGAA AATGATGCCA CATGACTACA
AACTCTCCCT AAATTTGACG TCTATTATAT
-2405 TTGGCATGGA GTCGATATTT TAATTTTAGT
TTTGTTGTTC TAAAGATTAA TATTATATAG
-2345 TAATGTTTTA CATTAATTTC ATAGTCTCCT
TTCCCCTCTC CCTATGGGTA AAAAGAAAGA
-2285 CATATTTAAA TCGATTTTTT AGATGGTCAA
TCTAAGCTTG CTTAGGGTTA ACCTATAAAA
-2225 GAATTTGTGT TGATTAGTAT CGAGATATAT
ACACTTCAAT ACTTAAGGTA TCAAATCAAG
-2165 TAATTGTTAA GTAATTGTTT ATATGGATAG
AAACGTGGGA AGAAAAGTAT ATACATAGAA
-2105 AAGTTGTACT TTGATTTTTT GGAAACTTTG
ATATTGACTC TTCAAAGGGT TGAATAAGCC
-2045 TCTCCAAACT CCATGGATGA CAATATGTTT
AACAAAAGTT AAAAATTGAT GTAATTCTTC
-1985 ACAAGTGGAC CAAAAATATT GATCTAATAT
GAGCAATAAT CGGGTACTTT TTCTATGCAT
-1925 ACATACCCAA AATAATAATA TTAATATGAA
TAATAATCAA CTTTAACCTT TTTTTTCTTT
-1865 TCGAAACGTG TTAAATTTTA ATGGGATGAA
ACAAGGGTTA CACATATCAT TCCTCATAAT
-1805 TACATCCTCT ATAAAGATGT GTGTTAATGT
TAATGTTAGA TATATAGAAA TTAAACTAGT
-1745 AATATATATT AAATCATGAT GATATTTTGG
AGAGAATGGA TCTATATCAA AGCACATAAG
-1685 AATCTTCTCC ATATAATTGT GATTGATATT
AATGGCCTTG AACAAATCAA CTTCACTGCC
-1625 ATTGCCTTCA AGTGTTGTTT CTTCTACAAC
ATTTCAATTC AACCCAATGC CCCATATCCT
-1565 TTCCCTTCCC CTTTTTTCTT TCTTTTGCCA
TTTTCATTTC TTAATTTCCA CCATTTGTAA
-1505 GACAGACAAA TGAGAAGTAA
AGAGATAAAC AAAAATCGAC ATACAAATTT
ACATTGTTCA
-1445 TTAACAATGT GCTAGCTTTA AAGCTTATAA
TCATCGGTAA GCAAAGAAAT TGTTTTTCTT
-1385 TTAATCTCAA GGAGAACATA GTTCATTATA
AATAAGGTAG GTAGAATTTT GTCTTTAAGG
-1325 TTCAAAATAA AGGTCCAAAT GAAAA-
CATAA TTAAACATAA TTTCAATATA ATTTAG-
GTCT
-1265 TAAAGGGGTA GCCCTAAAGC TCTTC-
GAAGA TCTTTTCCCC TGGATCACGA
CTCGTCTGGT
-1205 GTTACAGGGG CAAATCCAGG CTATA-
GATTT TTTAAAATAT GGTTATGACT CTTG-
GACTCT
-1145 ATGCTTGATC TTTCGAAGTA TCAAATACAC
TTTGANGTAT CTCAACCCCT AAAGTTGGCT
-1085 ACTTTCATTT TCTTTTTTAC GAAAGGTTCC
AACAAAATAA TGACATATCA CAAAAAAAGA
-1025 ATGAATTGTG CCCTACACTC AAGGAAG-
CAT TTTTAACTAT AAAAAATCAA
CAAGTCTCTT
-965 TTTAATAAAA TGTTTTTAAG TTAAACACTA
ATTATTATTG TACTTGATCG ATCAACTGTA
-905 GTAGGTAATT TGTTAAAACA TTTCATCTTA
AATAGTCAAT ATACAACTGG CACATGTTTG
-845 TGTAAAACAT TTCTTTATAG TTAGAGATTG
TTGGAATAAC TTATAACCAC TTAAGTTCAT
-785 AGCTTGTTCC ACGTTAAAAA ACTTATGAAT
GGATAAAATA GTCGTTAAGT CTTTTTGTTG
-725 TTGTTAGTAT CCTCTAATGA GTGGGTTATA
TACATACACA CATATAAAAG ATCACATTTT
-665 ACTCTTACTT TCTTTTCTTA AAAAACATCA
ACCTTCTTCA AGTCGAGAAA TATTCTTCAT
-605 AGTAATTAAA TAGATATGAG TTCTCGATTT
TCACTTGATT CCGGCCTTTC TCCAACGTGT
-545 GAACATTCGA TGTAGGTGTT ATGTTAAATC
TTTGAAAGCA ATCGATATAA ACAATTCAAA
-485 TGAGTATTTA TTGCCATAGA GTCGAAATGT
TTTCAAATTT ATTTTCAAAG TAATAGTAAT
-425 CGACACCAAA CGTTGGATTT AATGGTTATA
AACAATCAAA AGAAAAAAAG GAAAGGAAAG
-365 AATGACTTTT CATTTTCTGG GGTTTACTAC
ATTAAATAAT TACATGATAA TTTTTTTTCC
-305 ACATGATAAT TCCACGATGA ACAGAAAATA
AGANATGGCC AAAATTTCAT AGTTTGTGGA
-245 ATCTTCTTCA CCTTCCTTTA CCATTAACCA
ATCATCTTCA TAATCATCAA TTATCAGAAA
-185 ACGACCAAAG CTCTCTTCAT TTCAGTTTCA
TTTCACTCAC ATTTGCATTT GCATTCCCCC
-125 CCCCCCCCCC CCCCACCCCA TTATATAAAC
CAACCCCAAA TCTCTCTCCA ATTTCAACAC
-65 CAACAAACAC AACCAATAGA ACAAATATTA
ACCTTCTTTC CCTCTCTTTT GGAGGACTTC
-5 AAAAAATG

The putative start codon (ATG) of the galactinol synthase promoter is in boldface.

Fragments of the nucleotide sequence given as SEQ. ID. No. 2 which induce expression of heterologous DNA in transgenic plants are also suitable promoter DNA sequences for use in the DNA construct of the present invention.

The protein-encoding DNA molecule can be a DNA encoding for any of a wide variety of heterologous proteins. As used herein, the term "heterologous DNA" refers to a DNA segment that has been isolated or derived from one genotype, preferably amplified and/or chemically altered, and later introduced into a plant that may be a different genotype. Heterologous DNA does not generally include DNA of the same genotype, but "heterologous DNA" as used herein also includes DNA of the same genotype from which the amplified, chemically altered, or otherwise manipulated, DNA was first derived. Modification of the heterologous DNA sequence may occur, for example, by treating the DNA with a restriction enzyme to generate a DNA fragment which is capable of being operably linked to the promoter. Modification can also occur by techniques such as site-directed mutagenesis. "Heterologous DNA" also includes DNA that is completely synthetic, semi-synthetic, or biologically derived, such as DNA derived from RNA. "Heterologous DNA" also includes, but is not limited to, non-plant genes such as those from bacteria, yeasts, animals, or viruses; modified genes, portions of genes, chimeric genes, as well as DNA that encodes for amino acids that are chemical precursors or biologics of commercial value, such as polymers or biopolymers. Pool et al., "In Search of the Plastic Potato," *Science* 245:1187–1189 (1989), which is hereby incorporated by reference. Suitable heterologous DNA is any DNA for which expression in the minor vein phloem is beneficial to the plant or for which it is otherwise beneficial to have the DNA expressed selectively in the minor vein phloem of the plant.

According to one embodiment, the DNA molecule of choice encodes a heterologous protein that is toxic to insects. An example of such a protein is the toxin isolated from *Bacillus thuringiensis*. Under control of the GAS promoter, the toxin is selectively expressed in the leaf of the plant, and will not interfere with food crop or root system development.

There is a growing interest in using plants as an alternative to petrochemicals. The current emphasis is on increasing the production of lipids naturally produced by plants, and the need to increase the storage capacity of plants for useful products such as fatty acids and lipids. Accordingly, in another embodiment of the invention, the promoter of the present invention is operably linked to a heterologous gene comprising a coding sequence selected from a group of genes involved in fatty acid or lipid synthesis in plants and seed, and those that may be useful as precursors for bioplastic synthesis. U.S. Pat. No. 5,602,321 to Maliyakal, which is hereby incorporated by reference.

Examples of other DNA molecules that could be expressed in the present invention include, but are not limited to, hypersensitive response elicitor genes derived from bacterium, such as those encoding the harpin protein isolated from *Erwinia amylovora* and *Erwinia chrysanihemi* (U.S. Pat. No. 5,849,868 issued to Beer et al., which is hereby incorporated by reference), the hrpZ gene isolated from *Pseudomonas syringae* pv *syringae* (U.S. Pat. No. 5,858,768 issued to Collmer at al., which is hereby incorporated by reference), and viral replicase genes derived from plant pathogens, which confer pathogen resistance to transformed plants (U.S. Pat. Nos. 5,633,449 and 5,945,581, issued to Zaitlin et al., which are hereby incorporated by reference).

Additionally, DNA encoding for antibodies, vaccines or enzymes of any source are included as DNA molecules of choice for this invention. The promoter of the present invention may be used to direct expression of an antibody or vaccine to the leaf, from which it could be isolated or ingested directly.

Further examples of suitable DNA molecules of choice in the present invention include DNA which encodes for proteins associated with cell transporter mechanisms, and DNA encoding for receptor proteins.

The DNA construct of the present invention also includes an operable 3' regulatory region, selected from among those which are capable of providing correct transcription termination and polyadenylation of mRNA for expression in plant cells, operably linked to the a DNA molecule which encodes for a protein of choice. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," *Proc. Nat'l Acad. Sci. USA*, 80:4803–4807 (1983), which is hereby incorporated by reference) and the cauliflower mosaic virus 3' regulatory region (Odell, et al., "Identification of DNA Sequences Required for Activity of the Cauliflower Mosaic Virus 35S Promoter," *Nature*, 313(6005):810–812 (1985), which is hereby incorporated by reference). Virtually any 3' regulatory region known to be operable in plants would suffice for proper expression of the coding sequence of the DNA construct of the present invention.

The DNA molecule, the phloem-loading promoter, and a 3' regulatory region can be ligated together using well known molecular cloning techniques as described in Sambrook et al., *Molecular Cloning: A Laboratory Manual*, Second Edition, Cold Spring Harbor Press, NY (1989), which is hereby incorporated by reference.

The DNA construct can also include a DNA molecule encoding a secretion signal. A number of suitable secretion signals are known in the art and others are continually being identified. The secretion signal can be a DNA leader which directs secretion of the subsequently translated protein or polypeptide, or the secretion signal can be an amino terminal peptide sequence that is recognized by a host plant secretory pathway. The secretion-signal encoding DNA molecule can be ligated between the promoter and the protein-encoding DNA molecule, using known molecular cloning techniques as described in Sambrook et al., *Molecular Cloning: A Laboratory Manual*, Second Edition, Cold Spring Harbor Press, NY (1989), which is hereby incorporated by reference.

A further aspect of the present invention includes an expression system that includes a suitable vector containing a DNA construct of the present invention. In preparing the DNA construct for expression, the various DNA sequences may normally be inserted or substituted into a bacterial plasmid. Any convenient plasmid may be employed, which will be characterized by having a bacterial replication system, a marker which allows for selection in a bacterium and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTI, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of Agrobacterium tumefaciens. Fraley, et al., "Expression of Bacterial Genes in Plant Cells," *Proc. Nat'l Acad. Sci.*, 80: 4803–4807 (1983), which is hereby incorporated by reference.

Further improvement of this technique led to the development of the binary vector system. Bevan, M., "Binary Agrobacterium vectors for plant transformation," *Nucleic Acids Res.* 12:8711–8721 (1984), which is hereby incorporated by reference. In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly used vector is pBin19. Frisch, et al., "Complete sequence of the binary vector Bin19," *Plant Molec. Biol.* 27:405–409 (1995), which is hereby incorporated by reference. Any appropriate vectors now known or later described for plant transformation are suitable for use with the present invention.

U.S. Pat. No. 4,237,224 issued to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

A further aspect of the present invention includes a host cell which includes a DNA construct of the present invention. As described more fully hereinafter, the recombinant host cell can be either a bacterial cell (e.g., Agrobacterium) or a plant cell. In the case of recombinant plant cells, it is preferable that the DNA construct is stably inserted into the genome of the recombinant plant cell.

The DNA construct can be incorporated into cells using conventional recombinant DNA technology. Generally, this involves inserting the DNA construct into an expression vector or system to which it is heterologous (i.e., not normally present). As described above, the DNA construct contains the necessary elements for the transcription and translation in plant cells of the heterologous DNA molecule.

Once the DNA construct of the present invention has been prepared, it is ready to be incorporated into a host cell. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Springs Laboratory, Cold Springs Harbor, N.Y. (1989), which is hereby incorporated by reference. Suitable host cells include, but are not limited to, bacteria, virus, yeast, mammalian cells, insect, plant, and the like. Preferably the host cells are either a bacterial cell or a plant cell.

Accordingly, another aspect of the present invention relates to a method of making a recombinant plant cell. Basically, this method is carried out by transforming a plant cell with a DNA construct of the present invention under conditions effective to yield transcription of the DNA molecule in response to developmentally-induced activation of the phloem-specific promoter. Preferably, the DNA construct of the present invention is stably inserted into the genome of the recombinant plant cell as a result of the transformation.

One approach to transforming plant cells with a DNA construct of the present invention is particle bombardment (also known as biolistic transformation) of the host cell. This can be accomplished in one of several ways. The first involves propelling inert or biologically active particles at cells. This technique is disclosed in U.S. Pat. Nos. 4,945, 050, 5,036,006, and 5,100,792, all to Sanford, et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Another method of introducing the gene construct of the present invention into a host cell is fusion of protoplasts with other entities, either minicells, cells, lysosomes, or other fusible lipid-surfaced bodies that contain the chimeric gene. Fraley, et al., *Proc. Natl. Acad. Sci. USA*, 79:1859–63 (1982), which is hereby incorporated by reference.

The DNA construct of the present invention may also be introduced into the plant cells by electroporation. Fromm, et al., *Proc. Natl. Acad. Sci. USA*, 82:5824 (1985), which is hereby incorporated by reference. In this technique, plant protoplasts are electroporated in the presence of plasmids containing the DNA construct. Electrical impulses of high field strength reversibly permeabilize biomembranes allowing the introduction of the plasmids. Electroporated plant protoplasts reform the cell wall, divide, and regenerate.

Another method of introducing the DNA construct into plant cells is to infect a plant cell with *Agrobacterium tumefaciens* or *Agrobacterium rhizogenes* previously transformed with the DNA construct. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

Agrobacterium is a representative genus of the Gramnegative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences such as a DNA construct of the present invention can be introduced into appropriate plant cells by means of the Ti plasmid of *A. tumefaciens* or the Ri plasmid of *A. rhizogenes*. The Ti or Ri plasmid is transmitted to plant cells on infection by Agrobacterium and is stably integrated into the plant genome. Schell, J., *Science*, 237:1176–83 (1987), which is hereby incorporated by reference.

Plant tissue suitable for transformation include, but are not limited to leaf tissue, root tissue, meristems, zygotic and somatic embryos, megaspores and anthers.

After transformation, the transformed plant cells can be selected and regenerated.

Preferably, transformed cells are first identified using a selection marker simultaneously introduced into the host cells along with the DNA construct of the present invention. Suitable selection markers include, without limitation, markers coding for antibiotic resistance, such as the nptII gene which confers kanamycin resistance (Fraley, et al., *Proc. Natl. Acad. Sci. USA*, 80:4803–4807 (1983), which is hereby incorporated by reference) and the dhfr gene, which confers resistance to methotrexate (Bourouis et al., *EMBO J.* 2:1099–1104 (1983), which is hereby incorporated by reference). A number of antibiotic-resistance markers are known in the art and others are continually being identified. Any known antibiotic-resistance marker can be used to transform and select transformed host cells in accordance with the present invention. Cells or tissues are grown on a selection media containing an antibiotic, whereby generally only those transformants expressing the antibiotic resistance marker continue to grow. Similarly, enzymes providing for production of a compound identifiable by color change are useful as selection markers, such as GUS (β-glucuronidase), or luminescence, such as luciferase.

Also suitable as selection markers for the present invention are genes that cause the overproduction of a plant product, such as the cytokinin-synthesizing ipt gene from *A. tumefaciens*. Localized over-production of cytokinin can be determined by known methods, such as ELISA assay. Hewelt et al., "Promoter Tagging with a Promoterless ipt Gene Leads to Cytokine-induced Phenotypic Variability in Transgenic Tobacco Plants: Implications of Gene Dosage Effects," *Plant J.* 6:879–91 (1994), which is hereby incorporated by reference. The selection marker employed will depend on the target species; for certain target species, different antibiotics, herbicide, or biosynthesis selection markers are preferred.

Once a recombinant plant cell or tissue has been obtained, it is possible to regenerate a full-grown plant therefrom. Thus, the present invention also relates to a method of directing protein expression in minor vein phloem of a plant, wherein the phloem-specific DNA promoter is associated with a DNA molecule which encodes for either an endogenous or heterologous plant protein, such that the protein encoded is expressed in the minor vein phloem of a plant transformed with such a DNA construct.

The transgenic plant includes a DNA construct of the present invention, wherein the DNA promoter induces transcription of the protein-encoding DNA molecule in response to developmental activation of the promoter. Preferably, the desired heterologous DNA construct is stably inserted into the genome of the transgenic plant of the present invention.

Plant regeneration from cultured protoplasts is described in Evans, et al., *Handbook of Plant Cell Cultures Vol. 1:* (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference.

It is known that practically all plants can be regenerated from cultured cells or tissues, including but not limited to, all major species of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, sugarcane, and non-fruit bearing trees such as poplar, rubber, Paulownia, pine, and elm.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the DNA construct is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field.

Once transgenic plants of this type are produced, the plants themselves can be cultivated in accordance with conventional procedures. Alternatively, transgenic seeds are recovered from the transgenic plants. The seeds can then be planted in the soil and cultivated using conventional procedures to produce transgenic plants.

Recovery of the product of expression of any heterologous DNA of choice used in the present invention will depend on the exact nature of the product, and the technique chosen for recovery will be known to those skilled in the art.

EXAMPLES

Example 1

Plant Material Preparation

Melon (*Cucumis melo* cv. Hale's Best Jumbo; Vaughan's Seed Company, Downers Grove, Ill.), *Arabidopsis thaliana* var. Columbia, and *Nicotiana tabacum* cv. Petit Havana SR1 were used to prepare this invention. For melon DNA extraction, seed coats were removed, and seeds were germinated on damp filter paper in the dark for 7 to 9 days at 24° C. Arabidopsis plants were grown in artificial soil in 10-cm plastic pots covered with nylon window screen in a controlled environment chamber with a 16-hr/8-hr light/dark cycle at 21° C. Plants were fertilized twice a week with Peters 20:20:20 fertilizer (Scotts-Sierra Horticultural Products Co., Marysville, Ohio, USA). Tobacco plants were grown under similar conditions but at higher temperatures (25° C.).

Example 2

DNA Extraction and Southern Blotting

Genomic DNA was extracted from dark-grown melon seedlings by crude pelleting of nuclei (Bingham et al., "Cloning of DNA Sequences from the White Locus of *D. Melanogaster* by a Novel and General Method," *Cell* 25:693–704 (1981), which is hereby incorporated by reference) followed by a CTAB (cetyltrimethylammonium bromide) extraction procedure (Bernatzky et al., "Genetics of Actin-Related Sequences in Tomato," *Theor. Appl. Genet.* 72:314–321 (1986), which is hereby incorporated by reference). DNA was further purified by cesium chloride equilibrium density gradient centrifugation (Ausubel et al., "Current Protocols in Molecular Biology," New York: John Wiley & Sons, Inc. (1995), which is hereby incorporated by reference). Cesium chloride was removed from the DNA by dialysis against TE buffer, pH 8.0 (Sambrook et al., "Molecular Cloning: A Laboratory Manual," Cold Spring Harbor, N.Y.: Cold Spring Harbor Press (1989), which is hereby incorporated by reference). For Arabidopsis, DNA was extracted from young leaves using a miniprep procedure.

C. melo genomic DNA was digested with EcoRI restriction endonuclease and resolved by agarose gel electrophoresis. Southern blotting and hybridization were conducted using standard procedures (Sambrook et al., "Molecular Cloning: A Laboratory Manual," Cold Spring Harbor, N.Y.: Cold Spring Harbor Press (1989), which is hereby incorporated by reference). GAS-specific probes were constructed from a zucchini leaf GAS cDNA (CpGAS1), kindly provided by DuPont (Kerr et al., "Nucleotide Sequences of Galactinol Synthase from Zucchini and Soybean," International Patent Application Number PCT/US92/06057 (1992), which is hereby incorporated by reference). The CpGAS1 cDNA was originally isolated from a zucchini leaf cDNA expression library, and shown to have GAS catalytic activity (Kerr et al., "Nucleotide Sequences of Galactinol Synthase from Zucchini and Soybean," International Patent Application Number PCT/US92/06057 (1992), which is hereby incorporated by reference). A 3' GAS probe was made from an 0.8 kb HindIII fragment which included 697 bases of coding region and 90 bases downstream of the translational stop site. A 5' GAS probe was made from an 0.3 kb XabI/HindIII fragment which included 37 bases upstream of the translational start site and 300 bases of coding region. Probes were labeled with $\gamma^{32}$P-dCTP (DuPont-New England Nuclear, Boston, Mass.) using a random-primed DNA labeling kit (Boehringer-Mannheim, Indianapolis, Ind.), and unincorporated nucleotides were removed by passage over a microspin column filled with Sephadex G50 (Sigma, St. Louis, Mo.). Membranes were exposed to film (Jersey Lab Supply autoradiography film, Jersey Lab Supply, Livingston, N.J.) and autoradiographs were developed using standard procedures.

Example 3

Subgenomic Library

From a melon genomic DNA blot, a potential GAS gene was identified on a 6 kb EcoRI fragment. Fifty μg of DNA were digested to completion with EcoRI and the resulting fragments separated on an 0.68% Seaplaque GTG low-melting temperature agarose gel (FMC BioProducts, Rockland, Me.). Size fractionated fragments between 5 and 7 kb were isolated by electroelution (Sambrook et al., "Molecular Cloning: A Laboratory Manual," Cold Spring Harbor, N.Y.: Cold Spring Harbor Press (1989), which is hereby incorporated by reference) and ligated to EcoRI-cut and CIAP-treated λgt11 arms (Stratagene, LaJolla, Calif.) in a molar ratio of approximately 1:1. The ligation reaction was packaged in vitro using Gigapack III Gold packaging extract (Stratagene, LaJolla, Calif.) according to the manufacturer's instructions.

Phage were incubated with E. coli strain Y1088 and plated onto 150-mm NZY plates according to the manual provided (Stratagcne, LaJolla, Calif.). Lifts were made onto Magna Lift nylon membranes (Micron Separations Inc., Westboro, Mass.). The 5' GAS probe described above was used to screen the library and membranes were washed at high stringency (0.2×SSC, 0.5% SDS, 50° C.). Positive plaques from the first screen were purified by two additional rounds of screening using the same probe. Melon DNA from positive clones, isolated as EcoRI fragments, was subcloned into pBluescript II KS$^+$ (Stratagene, LaJolla, Calif.) digested with EcoRI. Positive clones contained the same 6 kb EcoRI segment of melon DNA. A positive clone, designated pSG8E, was sequenced at the Cornell DNA sequencing facility using a Perkin Elmer/Applied Biosystems Division 377 Automated DNA Sequencer, Dye Terminator chemistry, and AmpliTaq-FS DNA polymerase (Perkin-Elmer Applied Biosystems Division, Foster City, Calif.).

The 5' upstream GAS promoter from Cucumis melo has a nucleotide sequence corresponding to SEQ. ID. NO. 1.

Example 4

Vector Construction

Figure 2:
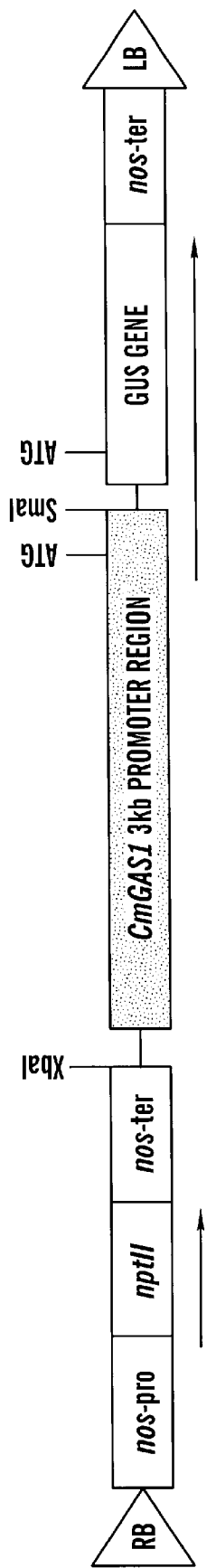
FIG. 2 is a diagram of the construction of the vector pSG3K101. A 3 kb XbaI/SmaI fragment upstream of the GAS gene and including the first 13 nucleotides of the coding region was fused in-frame to the uidA (GUS) gene in the binary vector pBI101.2, a promoterless GUS vector. The vector also contains the nptII gene for kanamycin resistance under control of a nopaline synthase promoter (nos-pro).

A putative translational start site was identified in the GAS equence by comparison to the CpGAS1 cDNA sequence (Kerr et al., "Nucleotide Sequences of Galactinol Synthase from Zucchini and Soybean," International Patent Application Number PCT/US92/06057 (1992), which is hereby incorporated by reference). The subgenomic GAS clone pSG8E was cut with XabI (3082 bases upstream of the putative translational start site) and PvuII (13 bases downstream of the putative translational start site). This fragment was ligated into the XabI and SmaI sites of pBI101.2 (a binary vector with a promoterless gusA gene; Clontech Laboratories Inc., Palo Alto, Calif.) to create pSG3K101. FIG. 2 shows the construction of the pSG3K101 vector Since the SmaI site of pBI101.2 is 17 bases upstream of the gusA translational start site, the gusA sequence is in-frame with the GAS start codon.

Example 5

Plant Transformation

Plasmid pSG3K101 was introduced into competent Agrobacterium tumefaciens strain GV3101 by a freeze-thaw procedure (Hooykaas, "Agrobacterium Molecular Genetics," in Gelvin, eds, Plant Molecular Biology Manual, Dordrecht, The Netherlands: Kluwer Academic Publishers, pp. A4: 1–13 (1988), which is hereby incorporated by reference). Stable transformants of Arabidopsis were obtained by infiltration of the plants with a solution of Agrobacterium as described by van Hoof et al., "Premature Nonsense Codons Decrease the Stability of Phytohemagglutinin mRNA in a Position-Dependent Manner," Plant J 10: 415–424 (1996), which is hereby incorporated by reference, except that no vacuum was used. Instead, rosettes and inflorescences were immersed in the Agrobacterium solution for 15 minutes. Plants were self-fertilized, and the resultant seed was plated on MS media containing 50 μg/ml kanamycin, with either 500 μg/ml vancomycin or 200 μg/ml cefotaxime to inhibit growth of bacteria. Transformants were transferred to artificial soil, allowed to self-pollinate, and seed was collected and planted on artificial soil for assays of reporter gene activity.

Nicotiana tabacum L. cv. petite havana SRI was transformed by cocultivation of leaf discs with Agrobacterium harboring pSG3K101 essentially as described by Horsch et al., "Transgenic Plants," Cold Spring Harbor Sym. Quant. Biol. 50: 433–7 (1985), which is hereby incorporated by refcrcnce. Except where noted, primary transformants were used for reporter gene assays.

Example 6

Histochemical Localization of GUS Expression

GUS staining was performed using the substrate 5-bromo-4-chloro-3-indolyl β-D-glucuronide (X-Gluc) according to the method described by Jefferson, "Assaying Chimeric Genes in Plants: The GUS Gene Fusion System," Plant Mol Biol. Reporter 5:387–405 (1987), which is hereby incorporated by reference, but with 3 mM potassium ferr- and ferrocyanide added to limit diffusion of GUS reaction products (Caissard et al., "Spurious Localizations of diX-Indigo Microcrystals Generated by the Histochemical GUS Assay," *Transgenic Res.* 3:176–181 (1994), which is hereby incorporated by reference). Samples were incubated in X-Gluc solution at 37° C. for 20 hours unless otherwise specified. After incubation, samples were cleared in ethanol. For resolution of specific cells, tissue was first stained and then fixed in glutaraldehyde by conventional techniques. The fixed tissue was dehydrated in ethanol and veins with good stain localization were identified, embedded in LR White resin, sectioned at 2 μm thickness, and observed under phase contrast without further staining.

Example 7

Radiolabeling

For [$^{14}$C]sucrose uptake studies, the adaxial surface of a leaf was abraded with carborundum and leaf discs were removed with a cork borer under the surface of 2(N-morpholino)ethanesulfonic acid (Mes) buffer (20 mM Mes plus 2 mM $CaCl_2$, pH 5.5, with NaOH). The discs were transferred, abraded side down, to the surface of fresh buffer containing [$^{14}$C]sucrose (1 mM; 30 kBq·$ml^{-1}$). Discs were incubated at room temperature on a shaker for 20 minutes, washed in three 10-minute changes of fresh buffer at room temperature, and frozen in powdered dry ice. Frozen tissue was lyophilized in a –30° C. chamber, pressed thin between steel plates in a large vice, and pressed against x-ray film (Hyperfilm-βmax, Amersham). In photoassimilate-labeling studies, an attached leaf was Benclosed in a Plexiglas cuvette and exposed to $^{14}CO_2$ generated in the barrel of a syringe from $Na_2^{14}CO_3$ (6.6×$10^5$ MBq·$mmol^{-1}$). Five minutes later the cuvette was removed and the leaf, still attached to the plant, was exposed to a 25-minute chase in room air before being frozen in liquid nitrogen. Radiolabeled compounds were extracted, passed through ion exchange resin (Turgeon, R. et al., "The Intermediary Cell: Minor-Vein Anatomy and Raffinose Oligosaccharide Synthesis in the Scrophulariaceae," *Planta* 191:446–456 (1993), which is hereby incorporated by reference) and analyzed by thin-layer chromatography as previously described (Turgeon, R. et al., "Sugar Synthesis and Phloem Loading in Coleus blumei Leaves," *Planta* 187:388–394 (1992), which is hereby incorporated by reference).

Example 8

Cloning and Sequencing the Galactinol Synthase Promoter

A Southern blot from melon genomic DNA digested with EcoRI was probed with the 5' zucchini leaf GAS cDNA probe. Three bands were visible, suggesting that galactinol synthase is a small gene family in melon. However, there was only one strongly hybridizing band, at 6 kb.

A melon subgenomic library was created and a clone containing a strongly hybridizing 6 kb EcoRI fragment was identified. The orientation of the clone was determined using probes derived from the 5' and 3' ends of the GAS cDNA on blots of various restriction digests. This clone contained approximately 3 kb and 0.5 kb of nonhybridizing DNA at the 5' and 3' ends of the DNA respectively. The 3 kb upstream region was sequenced, along with the start of the coding region. The gene was designated GAS.

Example 9

Expression Patterns in Arabidopsis

To visualize expression conferred by the GAS promoter, 3 kb of sequence upstream of the GAS open reading frame was cloned upstream of the gusA gene in pBI101.2 to create pSG3K101. Arabidopsis plants transformed with pSG3K101 were selected on media containing kanamycin. DNA from each of nine positively transformed lines was digested with BamHI and copy number was estimated by analysis of DNA blots probed with a 1 kb BamHI/PstI fragment from the CpGAS promoter (not shown).

Mature leaves, siliques, flowers, and whole plants were incubated in X-Gluc solution. Except where noted, results given are for low-copy-number lines; results from high-copy-number lines were the same except as discussed below. Wild-type controls were also stained following the same procedures; in no case was blue coloration observed in these tissues.

A typical shoot is shown in FIG. 3A. Staining was very apparent in the minor veins of cotyledons and mature leaves. In younger leaves, minor vein staining began at the lamina tips and progressed basipetally as the leaves aged, in the same pattern as the sink-source transition of photoassimilate transport (Turgeon, R., "The Sink-Source Transition in Leaves," *Ann. Rev. Plant Physiol. Plant Mol. Biol.* 40:119–138 (1989), which is hereby incorporated by reference). Hydathodes also stained (FIG. 3A). In all cases, GUS expression was absent or faint in the midrib and proximal ends of the secondary veins. Diffusion of reaction product was pronounced, especially in the cotyledons and first leaves, even though cyanide was included in the stain (Caissard et al., "Spurious Localizations of diX-Indigo Microcrystals Generated by the Histochemical GUS Assay," *Transgenic Res.* 3:176–181 (1994), which is hereby incorporated by reference).

To determine if the level of gusa expression was related to vein size, single leaves were cut into pieces and incubated in X-Gluc solution for different times. At 3 hours, staining was observed in the smallest veins and blind endings of the areoles (FIG. 3B) and became more evident in the larger veins at longer time periods (FIG. 3C). To facilitate penetration of substrate, similar experiments were conducted with leaf pieces cut 1 to 2 mm on a side. The same staining patterns were observed. Due to the diffusion of GUS reaction products, it was not possible to localize staining to individual cells in the phloem.

The time taken for stain to become visible in the veins, and ultimate staining intensity, were both proportional to transgene copy number. In high-copy number plants, blue color was also detected in the mesophyll, though it was much less intense than in the veins and took more than 20 hours to become apparent. Mesophyll staining was more apparent, and sometimes quite intense, in the cotyledons and in the first two true leaves than in the leaves subsequently produced. From these experiments, it cannot be established if this staining represents weak mesophyll expression in high-copy number lines, or diffusion from minor veins. It was also noted that damaged tissue demonstrated intense staining in the wounded area, presumably because GUS enzyme was released from the minor veins into the apoplast.

Veins in sepals and the vascular bundles of filaments were stained and veins in petals were faintly stained (FIG. 3D), but vascular bundles in the stem were unstained. Sepals are functionally associated with the flower of a plant, however, they are essentially leaf-like in anatomy and form, green in color, with a vascular system similar to a foliage leaf, though generally simpler in detailed structure. Esau, "Plant Anatomy," pp546–47, New York:John Wiley and Sons (1965). Once sepals, petals, and filaments had abscised, the vascular bundle scars stained blue; however, the rest of the silique, including seeds and remaining vasculature, remained unstained (not shown). To be sure that stain was able to penetrate the silique, we cut several longitudinally before staining; there was no difference in staining pattern. Light blue color was apparent in the cortex and vascular bundles of hypocotyls, though it stopped at the boundary between the shoot and the root. Occasional roots were stained in light patches, most often in lateral roots or toward the apex of the primary root (FIG. 3E). Some of the patches were in the cortex, but more were in the vasculature. This staining was much lighter than in the leaves and took much longer to develop.

Example 10

Expression Patterns in Tobacco

Growth on kanamycin was used to select for tobacco shoots transformed with pSG3K101. GUS staining was variable in the leaves of independent transformants, ranging from undetectable levels to easily discernible blue coloration in the minor veins (FIG. 3F). Expression patterns were studied in two independently derived, heavily-staining transformants.

In mature leaves, GUS activity was readily detected in the veins that define the areoles, and in the blind endings of the areoles: class V and VI veins, respectively (FIG. 3F). Class V veins are the most extensive in the leaf. Class IV veins, which define larger islands of the vein network, were stained blue in some regions but not in others. Class IV veins were often stained where class V veins merged with them (FIG. 3G). Class III veins, which define even larger segments of the vein network, and class I (midrib) and II veins (branching from the midrib), did not stain. As in Arabidopsis, staining increased in intensity toward the finest veins. No staining was detected in mesophyll cells.

To determine if promoter activity is developmentally regulated, tissue was sampled from the tip to base of leaves undergoing the sink-source transition. In relatively immature tissue, staining was first evident in isolated patches of class V veins, often at branch points (FIG. 3H). With increasing maturity, staining spread to more extensive regions of class V veins (FIG. 3I), then to class VI veins and to isolated regions of class IV veins. In general, staining became progressively more intense in the more distal (mature) regions of the leaf.

To look for staining in other regions of the plant, hand sections were taken from different tissues of the progeny of transformants, from seedling to flowering stages, and stained with GUS substrate without cyanide. Staining was not apparent in veins of leaves larger than Class IV, or in the midrib (FIG. 3K). No stain was detected in the apical meristem or in axial meristems. However, in mature flowers, some but not all of the smaller veins of the sepals were blue (not shown). No staining was present in any other tissues of mature flowers, including those of petals, stamens, carpels, or peduncles. Stem samples were free of stain except that in one sample of an older stem, irregular patches of stain were evident in the cortex and pit, especially the former. This staining was much lighter in intensity than that in the minor veins. No stain was detected in the vascular tissue of the root system, but stain was often detected in the apical meristems of roots.

The basipetal pattern of guva induction in maturing leaves of Arabidopsis and tobacco is similar to the sink-source transition of photoassimilate transport (Turgeon, R., "The Sink-Source Transition in Leaves," *Ann. Rev. Plant Physiol. Plant Mol. Biol.* 40:119–138 (1989), which is hereby incorporated by reference). The timing of initial GUS staining with respect to the onset of phloem loading was therefore studied in tobacco with radiolabeling experiments (FIG. 4). First, the position of the import-termination boundary in developing leaves was visualized by autoradiography after exposing mature leaves to $^{14}CO_2$ (Turgeon, R., "The Sink-Source Transition in Leaves," *Ann. Rev. Plant Physiol. Plant Mol. Biol.* 40:119–138 (1989), which is hereby incorporated by reference). Leaves of similar stages of development were then used for GUS-staining and phloem-loading studies. Discs of tissue were removed along the tip-to-base axis and were either stained for GUS or floated on [$^{14}C$]sucrose solution. In the experiment shown in FIG. 4, discs were removed from a leaf that had just stopped importing photoassimilate at its base. Weak, but nonetheless perceptible accumulation of radiolabel in veins was visible in the autoradiograph of a disc near the base of the leaf (FIG. 4D). Discs from more proximal tissue showed no evidence of loading, nor was there evidence of GUS staining in tissue from this region of the lamina. The first evidence of GUS staining, similar to that illustrated in FIG. 3H, was visible near the leaf tip, where the tissue was more mature. Phloem loading was more evident in tissue from this region (FIG. 3B) than from the base of the same leaf, though still not as strong as in discs taken from fully expanded, mature leaves (FIG. 3A); corresponding GUS staining pattern in FIG. 3G.

Example 11

GUS Expression in Different Companion Cells of Tobacco Minor Veins

Even when cyanide was included in the GUS solution, some diffusion of the stain was usually evident (FIG. 3G–I). However, on close inspection, stain was better localized in some veins than in others. This can be seen in FIG. 3G; there is no evidence of diffusion from the vein marked with an asterisk. This precise localization, and the regular and relatively simple structure of tobacco minor veins, were taken advantage of in studying expression in mature leaf tissue at the cell level. Stained tissue was fixed in glutaraldehyde, cleared, and examined with a stereo microscope. Veins with precise stain localization were excised and embedded for microscopy. In tobacco, the minor vein phloem of class V veins consists of three parenchyma cells that alternate in a ring with three companion cells, surrounding two sieve elements (Ding et al., "A Morphometric Analysis of the Phloem-Unloading Pathway in Developing Tobacco Leaves," *Planta* 176:307–318 (1988), Ding et al., "Accumulation of Mild and Severe Strains of Tobacco Mosaic Virus in Minor Veins of Tobacco," *Mol. Plant Microbe Interact.* 8:32–40 (1995), and Ding et al., "Tobamovirus and Potyvirus Accumulation in Minor Veins of Inoculated Leaves from Representatives of the Solanaceae and Fabaceae," *Plant Physiol.* 116:125–136 (1998), which are hereby incorporated by reference). In veins such as the one indicated in FIG. 3G, GUS stain was restricted to the two adaxial companion cells (FIG. 3J). No staining was detected in the abaxial companion cell or in the parenchyma cells in any of the veins examined. This staining pattern was consistent in the progeny of two independent transformants, whether the lower epidermis had, or had not been removed before staining.

Example 12

Absence of Galactinol Synthesis in Tobacco

To determine if mature tobacco leaves synthesize galactinol, attached leaves were exposed to $^{14}CO_2$ for 5 minutes and then to room air for a further 25 minute chase before extraction. No galactinol spot was present on autoradiographs of thin-layer chromatography (TLC) plates. In one quantitative analysis, the spot on the TLC plate corresponding to sucrose contained $1.47 \times 10^3$ Bq, whereas no activity above background (0.8 Bq) was detected in the galactinol spot.

In anatomical terms, minor veins do not have rib tissue that protrudes beneath the surface of the lamina (Esau, "Plant Anatomy," New York:John Wiley and Sons (1965), which is hereby incorporated by reference). From a physiological and developmental perspective, minor veins are those that are immature in sink leaves and do not participate in phloem unloading (Turgeon, R., "Phloem Unloading in Tobacco Sink Leaves: Insensitivity to Anoxia Indicates a Symplastic Pathway," *Planta* 171:73–81 (1987) and Roberts et al., "Phloem Unloading in Sink Leaves of *Nicotiana Benthamiana*: Comparison of a Fluorescent Solute with a Fluorescent Virus," *Plant Cell* 9:1381–1396 (1997), which are hereby incorporated by reference), but mature during the sink-source transition (Turgeon, R. et al., "Leaf Development and Phloem Transport in *Cucurbita Pepo*: Maturation of the Minor Veins," *Planta* 129:265–269 (1976), which is hereby incorporated by reference) and are believed to be the predominant site of photoassimilate loading into the translocation stream. The anatomical, developmental, and functional roles of leaf venation have been well studied in tobacco. The veins of tobacco leaves have been sub-divided into classes, based on cell numbers rather than branching pattern, which can be misleading (Ding et al., "A Morphometric Analysis of the Phloem-Unloading Pathway in Developing Tobacco Leaves," *Planta* 176:307–318 (1988), which is hereby incorporated by reference).

The different vein classes in tobacco appear to have specific roles, to a certain degree, in photoassimilate unloading and loading. Class III veins define large sectors of the lamina and are responsible for most photoassimilate unloading in sink leaves (Turgeon, R., "Phloem Unloading in Tobacco Sink Leaves: Insensitivity to Anoxia Indicates a Symplastic Pathway," *Planta* 171:73–81 (1987); Roberts et al., "Phloem Unloading in Sink Leaves of *Nicotiana Benthamiana*: Comparison of a Fluorescent Solute with a Fluorescent Virus," *Plant Cell* 9:1381–1396 (1997), which are hereby incorporated by reference). Class III veins probably have at most a limited role in loading once the leaf is mature, since they comprise a relatively small proportion of total vein length and the phloem is separated from mesophyll cells by several layers of parenchyma (Ding et al., "A Morphometric Analysis of the Phloem-Unloading Pathway in Developing Tobacco Leaves," *Planta* 176:307–318 (1988), which is hereby incorporated by reference). Class IV veins define smaller, but still relatively large islands of lamina and have one layer of intervening parenchyma in most cases (Ding et al., "A Morphometric Analysis of the Phloem-Unloading Pathway in Developing Tobacco Leaves," *Planta* 176:307–318 (1988), which is hereby incorporated by reference) thus they lack the required cumulative length to have more than a limited role in phloem loading. It appears that most phloem loading occurs in Class V veins, based on their great cumulative length and the fact that they outline almost all the areoles. Further, Class V veins lack the layer of parenchyma found in larger vein classes which could impede transport of carbohydrates from mesophyll to the sieve tubes. This is not to say that a small amount of phloem loading could not occur in larger vein classes; apoplastic phloem loading apparently involves the recruitment of a general mechanism of sucrose retrieval present in most, if not all cells. Therefore, there is a potential for flux of sucrose into the phloem all along the transport pathway.

The venation of Arabidopsis leaves has not been studied to the same extent. Nonetheless, all but the largest veins are embedded directly in the mesophyll, without intervening layers of parenchyma, and thus appear capable of phloem loading (Haritatos et al., "Minor Vein Structure and Sugar Transport in *Arabidopsis Thaliana*," *Planta* (in press) (2000), which is hereby incorporated by reference).

It seemed reasonable that the GAS promoter would confer gene expression specifically in the subset of minor veins where phloem loading occurs. GAS catalyzes the first committed step leading to the production of raffinose and stachyose for export. The synthesis of these sugars is apparently an integral part of the phloem loading mechanism in cucurbits and other plants with intermediary cells (Turgeon, R., "Phloem Loading and Plasmodesmata," *Trends in Plant Science* 1:403–441 (1996), which is hereby incorporated by reference). Intermediary cells are specialized companion cells of minor veins that are found only in plants that export raffinose-family oligosaccharides (RFOs). In leaves, synthesis of RFOs takes place in intermediary cells, but not in companion cells of major veins, or in the "ordinary" companion cells of minor veins (Holthaus et al., "Distribution and Immunolocalization of Stachyose Synthase in *Cucumis Melo* L," *Planta* 185:479–486 (1991), and Beebe et al., "Localization of Galactinol, Raffinose, and Stachyose Synthesis in *Cucurbita pepo* Leaves," *Planta* 188:354–361 (1992), which are hereby incorporated by reference). To determine the tissue and cell specificity of the GAS promoter, we cloned 3 kb of sequence upstream of the GAS open reading frame and analyzed the expression pattern this element confers on the gusA reporter gene in Arabidopsis and tobacco.

The observed expression pattern correlates well with the size of veins thought to be actively involved in phloem loading. As discussed above, there may be some phloem loading, or at least retrieval of leaked sucrose, in larger veins. Indeed, the promoter of the Arabidopsis SUC2 sucrose-H+symporter directs expression to source leaf phloem and also to the phloem of larger veins and other tissues (Truernit et al., "The Promoter of the *Arabidopsis Thaliana* SUC2 Sucrose-H+Symporter Directs Expression of Beta-Glucuronidase to the Phloem: Evidence for Phloem Loading and Unloading by SUC2," *Planta* 196:564–570 (1995), which is hereby incorporated by reference). The unique feature of the GAS promoter is that the conferred expression pattern reveals the subset of minor veins that appear, on the basis of overall length and structural characteristics, to be most actively devoted to the loading function.

How well does the expression pattern of the GAS-GUS construct correlate with phloem loading activity? Unfortunately, it is not possible to answer this question with certainty: transport along the phloem is rapid and when loading studies are conducted with radiolabeled sugars or $^{14}CO_2$, the label quickly disperses throughout veins of all sizes. It is known from radiolabeling studies that there is a substantial lag between the termination of import and the beginning of export in leaf tissue undergoing the sink-source transition (Turgeon, R. et al., "Leaf Development and Phloem Transport in Cucurbita Pepo: Carbon Economy,"

Planta 123:53–62 (1975), which is hereby incorporated by reference). Since GAS is involved in export, it was expected that GAS-GUS expression would not correlate with cessation of import. However, there also appears to be a lag between the onset of phloem loading in tobacco leaves, as revealed by [$^{14}$C]sucrose accumulation, and the initial expression of the GAS-GUS construct. This lag may be due, in part, to differences in sensitivity between the autoradiographic technique and GUS staining. Alternatively, since the GAS promoter is heterologous in tobacco, a greater accumulation of trans-acting factors may be required for activation. It should be possible to distinguish between the contributions of these factors to the lag period once melon plants transformed with GAS-GUS become available.

Within class V tobacco minor veins, the promoter is active in only two of six cells that customarily surround the two sieve elements. The two cells in these positions have been identified as companion cells since they do not plasmolyze when the tissue is incubated in 1 M sorbitol (Ding et al., "Accumulation of Mild and Severe Strains of Tobacco Mosaic Virus in Minor Veins of Tobacco," *Mol. Plant Microbe Interact*. 8:32–40 (1995), and Ding et al., "Tobamovirus and Potyvirus Accumulation in Minor Veins of Inoculated Leaves from Representatives of the Solanaceae and Fabaceae," *Plant Physiol*. 116:125–136 (1998), which are hereby incorporated by reference). However the lower (most abaxial) cell in the vein is also considered to be a companion cell by the same criterion, and it does not stain in the minor veins of two lines of tobacco independently transformed with GAS-GUS. Therefore, the promoter is either differentially expressed in the various companion cells of the same vein, or the most abaxial of these cells is not a true companion cell. The latter interpretation seems unlikely since the lower of the two sieve elements usually appears to be in close juxtaposition with the cell in question, thus implying an ontogenetic relationship. It is worth noting that galactinol synthase is immunolocalized to intermediary cells of cucurbits, but not to "ordinary" companion cells in the same minor veins (Beebe et al., "Localization of Galactinol, Raffinose, and Stachyose Synthesis in *Cucurbita pepo* Leaves," *Planta* 188:354–361 (1992), which is hereby incorporated by reference) a finding that is also consistent with highly regulated, differential expression of the gene for this enzyme in closely associated companion cells.

Since the GAS promoter from melon confers a similar expression pattern in Arabidopsis and tobacco, it appears to respond to conserved trans-acting signals. This is true even though the amount of galactinol produced by these three species differs considerably. Melon transports high levels of raffinose and stachyose and produces almost as much galactinol as raffinose (Haritatos et al., "Raffinose Oligosaccharide Concentrations Measured in Individual Cell and Tissue Types in *Cucumis melo* L. Leaves: Implications for Phloem Loading," *Planta* 198:614–622 (1996), which is hereby incorporated by reference). We could not detect synthesis of any galactinol in tobacco. This suggests that the trans-acting factor(s) that activate the GAS promoter in tobacco regulate the expression of other genes involved in companion cell function and photoassimilate export.

Significantly, these findings indicate that the somewhat arbitrary definition of a "minor vein" network within the leaf is supported at the molecular genetic level. That is, different vein classes, and different companion cells within the same vein, apparently have unique compliments of trans-acting factors and consequently, have distinct cascades of gene expression. Since the phloem network is central to the growth and development of plants, this genetic heterogeneity deserves further study.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated DNA promoter capable of inducing expression of a protein encoded by a DNA molecule operably associated with the promoter, wherein the DNA promoter causes the protein to be expressed in one or more of minor vein phloem of a plant leaf, companion cells of minor vein phloem of a plant leaf, sepals of a plant, or root tips of a plant, and wherein the DNA promoter is a nucleic acid selected from the group consisting of a nucleotide sequence comprising SEQ. ID. No. 1, a nucleotide sequence comprising bases −1764 to +12 of SEQ. ID. No. 1, a nucleotide sequence comprising bases −1338 to +12 of SEQ. ID. No. 1, a nucleotide sequence comprising bases −1149 to −1078 of SEQ. ID. No. 1, and a nucleotide sequence comprising SEQ. ID. No. 2.

2. An isolated DNA promoter according to claim 1, wherein the DNA promoter induces expression of the protein encoded by the DNA molecule in minor vein phloem of a mature plant leaf.

3. An isolated DNA promoter according to claim 1, wherein the DNA promoter induces expression of the protein encoded by the DNA molecule in companion cells of the minor vein phloem of a plant leaf.

4. An isolated DNA promoter according to claim 1, wherein the DNA promoter induces expression of the protein encoded by the DNA molecule in sepals of the plant.

5. An isolated DNA promoter according to claim 1, wherein the DNA promoter induces expression of the protein encoded by the DNA molecule in root tip s of the plant.

6. An isolated DNA promoter according to claim 1, wherein the DNA promoter is isolated from melon.

7. An isolated DNA promoter according to claim 1, wherein the DNA promoter drives expression of galactinol synthase in plants.

8. An isolated DNA promoter according to claim 7, wherein the DNA molecule is isolated from a GAS gene.

9. A DNA construct comprising:
   a DNA molecule encoding a protein;
   a DNA promoter according to claim 1, wherein the DNA promoter is operably linked 5' to the DNA molecule encoding a protein to induce transcription of the DNA molecule encoding a protein; and
   a 3' regulatory region operably linked to the DNA molecule encoding a protein.

10. A DNA construct according to claim 9, wherein the DNA promoter is isolated from melon.

11. A DNA construct according to claim 9, wherein the DNA promoter drives expression of galactinol synthase.

12. A DNA construct according to claim 9, wherein the DNA promoter molecule is isolated from a GAS gene.

13. A DNA construct according to claim 9, wherein the DNA molecule encodes a protein endogenous to plants, said protein selected from the group consisting of enzymes, precursors of fatty acids, precursors of lipids, transporters, and receptors.

14. A DNA construct according to claim 9, wherein the DNA molecule encodes a protein heterologous to plants, said protein selected from the group consisting of pesticides, insecticides, biopolymers, enzymes, plastics precursors, chemical precursors, precursors of lipids, transporters, and receptors.

15. An expression system comprising a vector into which is inserted a DNA construct according to claims 9.

16. A host cell comprising a DNA construct according to claim 9.

17. A host cell according to claim 16, wherein the host cell is a bacterial cell or a plant cell.

18. A host cell according to claim 17, wherein the host cell is Agrobacierium.

19. A host cell according to claim 17, wherein the host cell is a plant cell.

20. A host cell according to claim 19, wherein the host cell is a plant cell selected from a group consisting of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, sugarcane, and non-fruit bearing trees.

21. A transgenic plant comprising a DNA construct according to claim 9.

22. A transgenic plant according to claim 21, wherein the DNA promoter is isolated from melon.

23. A transgenic plant according to claim 21, wherein the DNA promoter drives expression of galactinol synthase.

24. A transgenic plant according to claim 23, wherein the DNA promoter is isolated from a GAS gene.

25. A transgenic plant according to claim 1, wherein the DNA promoter induces expression of the protein encoded by the DNA molecule in the minor vein phloem of a mature plant leaf.

26. A transgenic plant according to claim 21, wherein the DNA promoter induces expression of the protein encoded by the DNA molecule in companion cells of the minor vein phloem of the plant.

27. A transgenic plant according to claim 21, wherein the DNA promoter induces expression of the protein encoded by the DNA molecule in sepals of the plant.

28. A transgenic plant according to claim 21, wherein the DNA promoter induces expression of the protein encoded by the DNA molecule in root tips of the plant.

29. A transgenic plant according to claim 21, wherein the DNA molecule encodes a protein endogenous to plants, said protein selected from the group consisting of enzymes, precursors of fatty acids and precursors of lipids, transporters, and receptors.

30. A transgenic plant according to claim 21, wherein the DNA molecule encodes a protein heterologous to plants, said protein selected from the group consisting of pesticides, insecticides, biopolymers, enzymes, plastics precursors, chemical precursors, petrochemical precursors, precursors of lipids, transporters, and receptors.

31. A transgenic plant according to claim 21, wherein the transgenic plant is selected from a group consisting of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, sugarcane, and non-fruit bearing trees.

32. A transgenic plant seed comprising a DNA construct according to claim 9.

33. A transgenic plant seed according to claim 32, wherein the transgenic plant seed is selected from a group consisting of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, sugarcane, and non-fruit bearing trees.

34. A method of directing protein expression in one or more of minor vein phloem, sepals, or root tips of plants, said method comprising:

transforming a plant cell with a DNA construct according to claim 9 and regenerating a plant from the transformed plant cell, wherein expression of the DNA molecule, under control of the DNA promoter, occurs in minor vein phloem, sepals, or root tips of the plant.

35. A method according to claim 34, wherein said transforming is carried out under conditions effective to insert the DNA construct into the genome of the plant cell.

36. A method according to claim 35, wherein said transforming is Agrobacterium mediated.

37. A method according to claim 35, wherein said transforming comprises:

propelling particles at the plant cell under conditions effective for the particles to penetrate into the cell interior and introducing an expression vector comprising the DNA construct into the plant cell interior.

38. A method of making a transgenic plant comprising:

transforming a plant cell with a DNA construct according to claim 9 and regenerating a plant from the transformed cell.

39. A method according to claim 38, wherein said transforming is carried out under conditions effective to insert the DNA construct into the genome of the plant cell.

40. A method according to claim 38, wherein said transforming is Agrobacterium mediated.

41. A method according to claim 38, wherein said transforming comprises:

propelling particles at the plant cell under conditions effective for the particles to penetrate into the cell interior and introducing an expression vector comprising the DNA construct into the plant cell interior.

42. A host cell according to claim 20, wherein the host cell is a cell of a non-fruit bearing tree selected from the group consisting of poplar, rubber, Paulownia, pine, and elm.

43. A transgenic plant according to claim 31, wherein the transgenic plant is a non-fruit bearing tree selected from the group consisting of poplar, rubber, Paulownia, pine, and elm.

44. A transgenic plant seed according to claim 33, wherein the transgenic plant seed is a seed of a non-fruit bearing tree selected from the group consisting of poplar, rubber, Paulownia, pine, and elm.

* * * * *

SEQUENCE LISTING

<160> NUMBER OF SEQ ID NOS: 2

<210> SEQ ID NO 1
<211> LENGTH: 3343
<212> TYPE: DNA
<213> ORGANISM: Cucumis melo

<400> SEQUENCE: 1

```
gagctccacc gcggtggcgg ccgctctaga actagtggat cccccgggct gcaggaattc        60
tagatgactt ggattaattc tctaacaaga atttagttta attgacattt gtatgtttga       120
ggactaagag gactttagtt ttaatttcta atctaatttg tactagaaaa gaaaaaaaaa       180
gagtcggatt aattctctac cattgagtgg aggatacttg gatgcagttc aagttctcat       240
ctctccaatt tgtcacgtga cagcggatga ttaagcatat gagtaggctg caaaagatta       300
tagacgtaga agatgatacc caatacaaag gcgtaacttt tcccggatga cttttatact       360
ctttacaaaa ttggaagtcc tattctatct acatcttaat ttccagttgt tataatgaag       420
aatagtctga aaatgatatc aatttttttct ttctcaatac cattcaatta cgttaagatt       480
attaggagct gccattatta ttattattat tgttgttgtt attattatta ttatgcaacc       540
aagtttgatt tgaaattgtt tgccaaattt tactccaatt tgatgttgtt taattacttt       600
```

-continued

```
agatggtata ataagaatga agttgaattt aaagaaaaga aacaaagctt gaaagaatgg      660
aatacttagg tgtagaagaa gacaacgtat ttataacgtc gtatagtgtt aataaaaatg      720
cacacatttg gatgcccttt atgctttctt agaggtcaga ctttcccaca aaggctaagg      780
tgattcaatc gtgtgggaca tcttgttctc ccatttgatt ctcgttttca ttagaccaaa      840
attaacaaaa aaatagtaat aattctattc tttttaaagt ttgtgatatt acggtttatc      900
ctttgttaaa aaagtttatc tttgaatgta agaatttgat agaatgttga atgaaaatta      960
agattttgaa aagttttgct gaatttcaaa taatataact ctctaactttt ggtttaggaa     1020 aattaagtga tgacaattat ctctattaga attagtatta taagtgatat ttgagttatg     1080
cacttgactt ggtcgtgttg gtaaattctt tggatacaga acaaaagaag ttgcatgcca     1140
agaaagattt ctaatagata tggtgagata tgtggccgtt ggctctattg gattggtggt     1200
atgttccaga gaagaggagt gcgtatggat acgacctagg tggataaatg attatatgag     1260
gagatggtaa ttttatgaaa tgtgttagag ctttgatgtt aatatatatt ttttaagtgt     1320
gttttgtgat cgatggtatt agatgagttc cttattaaac atgttttctt gttttctcg      1380 aggtggggtt ctcaacactt ggtaacatgc atcatgtcca cgagatgttc ttcatcttat     1440
ctcttgtaat attatatatg atatctcaca caatacaggt tcgtctgaaa aatctttctt     1500
tatttgaaat tttttaggta tttattcttg aggattttt tattcttaag taaagtgttc      1560
atgatttgaa gttagaaata taggagttat ttttaagaga gagtctcaca ctcaaaggga     1620
gtctaaatat ctttttttact aatttaggtt gtgtaataac cttgtattta tcgataagta    1680
tcacgatgta atcatttaac tatctattaa cgaaaatctt ttttaggaca cgttgcctcc    1740
tagatagatg caagttgtat tgcaaaactt gtactctgtt ttttagtttt ttacatgttt    1800
tactttagaa ctaaacctaa gttatgttat gtgtcaaata aacttctta aaataatatt     1860 aaaacttctc aaaataatag gaaaaaaaag aaaaatttca aatttaatat atatatatat    1920
atattgtaat attagctttc attatcattg aattaaaaat tgcatataca agaatcgaat    1980
aatgtggaga agtagttttt cctttttcaa ctttgtgtag aggctaagtc tctaaaatat    2040
tggcttcgac tttgtacttt tgggatccgc caccacaatc agacaaactt ccatttgatc    2100
attaccttta tcgaatcaaa ttcttcccct tccaatctgt cacaattttg aacataccat    2160
ccaccttctg atttttgat tctaaataaa cctattagc agagattttt aaaattagta     2220
ttaaattata ccaaataccc taatgaactt tttcaatagt ttttctattt tatttttttt    2280
ttcttttgtg tgtatgagtt ttttcaccac cattagaaaa cacatttgaa atatacagaa    2340
ccaaattgtt taatttgaat tggttttcca taccatttttt acaaaataca tagtataacc    2400
aaaagaacta tagttttaag tagtgtataa tagtttaatt ttaaagacaa agaactaaac    2460
aataatcatt atcaaaaaca ctaccttaaa acagaattga aatcaaatcc atttgtttag    2520
gaatatatat atatatatat atatatataa tatagtatca taatatataa aaaaaatgtc    2580
aaaatctgag attctttgat cctccctaaa ttgtccattt ttgtcttgcc tacaaacttg    2640 caaaaagaa aaaaaaaag gttcatagat agaaatgacc cataattgaa tcataaagca     2700
ataaggatat acaaaattat tatatccaag agggatgaga gataatctta aagtgcaaa    2760 agatcttct tattgatgga agaagagaat acaaactctt ccaacttttg atcaaaatgc     2820
ccataatgcc ctccatctca ccttaaagat aggatattcc aagtcatatt catcccacca    2880
ataccaatat ctaaaataat aagtaacaaa taattacaat tacaaatata aagtgcatag    2940
```

-continued

| | |
|---|---|
| aaattaaact tagggtatg tataaactta aaacaatgtt ccccaaggct ctataaatag | 3000 |
| cctccttccc atcccttcac aactcaagct tgaaggacta aaacaagaac ttgtaagctt | 3060 |
| gcccttctta ttaagtcctt cttgcctccc ttccttcgga gagaaaaaac ttttgttgtt | 3120 |
| tcaaaagcac caaagtcaat atgtctcctg cagctgcccc agaaagtgcc attgagtcaa | 3180 |
| ctgacgctcc caagagggcg tacgtgacgt tcttagctgg taatggtgac tactggaaag | 3240 |
| gtgtagttgg attggcaaag ggtctcagaa aggtcaaagc cgcctaccct ctcattgtcg | 3300 |
| ctgtccttcc tgatgttcct gaagatcatc gccaatcctc gag | 3343 |

<210> SEQ ID NO 2
<211> LENGTH: 3008
<212> TYPE: DNA
<213> ORGANISM: Cucumis melo
<220> FEATURE:
<221> NAME/KEY: unsure
<222> LOCATION: ()
<223> OTHER INFORMATION: N at any position in this sequence is either A,
      C, G, or T

<400> SEQUENCE: 2

| | |
|---|---|
| tagttccggt cctgcnagac tggcccccgc tcgaaacctc cctgggtgtg agggtaggat | 60 |
| tgtccacatt atggaccgtc tcattctctc tctatgtcgt tctcgttagt atcaacttgc | 120 |
| aacttgtatt acgctagcaa ttataacgac tcaccaaaat ttacttcttc actacttctt | 180 |
| cacgtatctc ttatttgaag aaaaaaaagt aaaaataaaa tataagttat acatagcata | 240 |
| tccgaagtga ttctaaaata agtaaaatca ctttgaatca cacttttaat cattcaagac | 300 |
| ctatttaatg tttaatcttt agattttat atatactttt catatggtta aaattaatttt | 360 |
| taaatgatta aagaaatttt tcaagtgatt ttgaccattt taaaatagtt atgcccaaat | 420 |
| atatcattac acatctctta attttttcaag ttcgaagagt tttgaagaat ttgttttctc | 480 |
| aacatgatgg gctcccccctc ttgtcccctc tcaaagccat catttatcaa gtgaaagaat | 540 |
| tgcacttgaa aatgatgcca catgactaca aactctccct aaatttgacg tctattatat | 600 |
| ttggcatgga gtcgatattt taattttagt tttgttgttc taaagattaa tattatatag | 660 |
| taatgtttta cattaatttc atagtctcct ttccccctctc cctatgggta aaaagaaaga | 720 |
| catatttaaa tcgatttttt agatggtcaa tctaagcttg cttagggtta acctataaaa | 780 |
| gaatttgtgt tgattagtat cgagatatat acacttcaat acttaaggta tcaaatcaag | 840 |
| taattgttaa gtaattgttt atatggatag aaacgtggga agaaaagtat atacatagaa | 900 |
| aagttgtact ttgatttttt ggaaactttg atattgactc ttcaaagggt tgaataagcc | 960 |
| tctccaaact ccatggatga caatatgttt aacaaaagtt aaaaattgat gtaattcttc | 1020 |
| acaagtggac caaaaatatt gatctaatat gagcaataat cgggtacttt ttctatgcat | 1080 |
| acatacccaa aataataata ttaatatgaa taataatcaa ctttaacctt ttttttcttt | 1140 |
| tcgaaacgtg ttaaattta atgggatgaa acaagggtta cacatatcat tcctcataat | 1200 |
| tacatcctct ataagatgt gtgttaatgt taatgttaga tatatagaaa ttaaactagt | 1260 |
| aatatatatt aaatcatgat gatattttgg agagaatgga tctatatcaa agcacataag | 1320 |
| aatcttctcc atataattgt gattgatatt aatggccttg aacaaatcaa cttcactgcc | 1380 |
| attgccttca agtgttgttt cttctacaac atttcaattc aacccaatgc cccatatcct | 1440 |
| ttcccttccc cttttttctt tcttttgcca ttttcatttc ttaatttcca ccatttgtaa | 1500 |
| gacagacaaa tgagaagtaa agagataaac aaaaatcgac atacaaattt acattgttca | 1560 |

-continued

```
ttaacaatgt gctagcttta aagcttataa tcatcggtaa gcaaagaaat tgtttttctt    1620
ttaatctcaa ggagaacata gttcattata aataaggtag gtagaatttt gtctttaagg    1680
ttcaaaataa aggtccaaat gaaaacataa ttaaacataa tttcaatata atttaggtct    1740
taaaggggta gccctaaagc tcttcgaaga tcttttcccc tggatcacga ctcgtctggt    1800
gttacagggg caaatccagg ctatagattt tttaaaatat ggttatgact cttggactct    1860
atgcttgatc tttcgaagta tcaaatacac tttgangtat ctcaacccct aaagttggct    1920
actttcattt tcttttttac gaaaggttcc aacaaaataa tgacatatca caaaaaaaga    1980
atgaattgtg ccctacactc aaggaagcat ttttaactat aaaaaatcaa caagtctctt    2040
tttaataaaa tgtttttaag ttaaacacta attattattg tacttgatcg atcaactgta    2100
gtaggtaatt tgttaaaaca tttcatctta aatagtcaat atacaactgg cacatgtttg    2160
tgtaaaacat ttctttatag ttagagattg ttggaataac ttataaccac ttaagttcat    2220
agcttgttcc acgttaaaaa acttatgaat ggataaaata gtcgttaagt cttttttgttg   2280 ttgttagtat cctctaatga gtgggttata tacatacaca catataaaag atcacatttt    2340
actcttactt tcttttctta aaaaacatca accttcttca agtcgagaaa tattcttcat    2400
agtaattaaa tagatatgag ttctcgattt tcacttgatt ccggcctttc tccaacgtgt    2460
gaacattcga tgtaggtgtt atgttaaatc tttgaaagca atcgatataa acaattcaaa    2520
tgagtattta ttgccataga gtcgaaatgt tttcaaattt attttcaaag taatagtaat    2580
cgacaccaaa cgttggattt aatggttata aacaatcaaa agaaaaaaag gaaaggaaag   2640
aatgactttt cattttctgg ggtttactac attaaataat tacatgataa ttttttttcc    2700
acatgataat tccacgatga acagaaaata aganatggcc aaaatttcat agtttgtgga    2760
atcttcttca ccttccttta ccattaacca atcatcttca taatcatcaa ttatcagaaa    2820
acgaccaaag ctctcttcat ttcagtttca tttcactcac atttgcattt gcattccccc    2880
cccccccccc ccccacccca ttatataaac caacccaaa tctctctcca atttcaacac    2940
caacaaacac aaccaataga acaaatatta accttctttc cctctctttt ggaggacttc    3000
aaaaaatg                                                            3008
```